US012746307B2

(12) United States Patent
Karlin

(10) Patent No.: US 12,746,307 B2
(45) Date of Patent: Sep. 29, 2026

(54) CARTILAGE TREATMENT FOR USE IN EYELID RECONSTRUCTION

(71) Applicant: The Regents of the University of California, Oakland, CA (US)

(72) Inventor: Justin Karlin, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 406 days.

(21) Appl. No.: 18/288,321

(22) PCT Filed: Apr. 29, 2022

(86) PCT No.: PCT/US2022/026938
§ 371 (c)(1),
(2) Date: Oct. 25, 2023

(87) PCT Pub. No.: WO2022/232516
PCT Pub. Date: Nov. 3, 2022

(65) Prior Publication Data
US 2024/0207484 A1 Jun. 27, 2024

Related U.S. Application Data

(60) Provisional application No. 63/182,278, filed on Apr. 30, 2021.

(51) Int. Cl.
*A61L 27/00* (2006.01)
*A61F 11/00* (2022.01)
(Continued)

(52) U.S. Cl.
CPC ................................ *A61L 27/3612* (2013.01)

(58) Field of Classification Search
None
See application file for complete search history.

(56) References Cited

U.S. PATENT DOCUMENTS 5,336,616 A * 8/1994 Livesey .............. A61L 27/3604 435/395
6,166,288 A * 12/2000 Diamond ............. C07K 14/705 800/25
(Continued)

FOREIGN PATENT DOCUMENTS

AU 2006200194 A1 * 2/2006
CA 2299956 A1 * 9/2001 ............. A61K 35/60
(Continued)

OTHER PUBLICATIONS

International Search Report & Written Opinion, dated Aug. 10, 2022, from corresponding International Application No. PCT/US22/26938.
(Continued)

*Primary Examiner* — Ann Hu
(74) *Attorney, Agent, or Firm* — Mark S. Cohen; PEARL COHEN LLP

(57) ABSTRACT

The present disclosure relates to methods for preparing ear cartilage for eyelid reconstruction, including upper eyelid reconstruction, after trauma, disease, or tumor excision. The present disclosure also relates to compositions, uses, and methods for reconstructing an eyelid. The present disclosure also relates to kits for preparing ear cartilage for eyelid reconstruction. The disclosed compositions, uses, kits, and methods may also be used for autograft, allograft, isograft, and xenograft transplantation, for stored or banked grafts, and for other therapeutic uses.

15 Claims, 4 Drawing Sheets

Specification includes a Sequence Listing.

(51) Int. Cl.
*A61L 2/14* (2006.01)
*A61L 27/36* (2006.01)

(56) References Cited

U.S. PATENT DOCUMENTS

| | | | | |
|---|---|---|---|---|
| 6,239,106 | B1 * | 5/2001 | Voerman | C07K 14/815<br>435/320.1 |
| 6,635,285 | B2 * | 10/2003 | Dupont | A61K 35/60<br>530/400 |
| 10,973,953 | B1 * | 4/2021 | Semler | A61L 27/38 |
| 2008/0077251 | A1 * | 3/2008 | Chen | A61F 2/30756<br>623/23.72 |
| 2016/0114080 | A1 * | 4/2016 | Sun | A61L 27/362<br>435/267 |
| 2017/0049930 | A1 * | 2/2017 | Nasert | B29B 13/04 |
| 2023/0295573 | A1 * | 9/2023 | Athanasiou | C12N 5/0655<br>435/366 |

FOREIGN PATENT DOCUMENTS

| | | | | |
|---|---|---|---|---|
| EP | 1410810 A1 * | 4/2004 | | A61L 27/3604 |
| WO | WO 96/12804 | 5/1996 | | |
| WO | WO-2008002059 A1 * | 1/2008 | | A61P 3/10 |

OTHER PUBLICATIONS

Yamamoto et al., "Eyelid Reconstruction Using Oral Mucosa and Ear Cartilage Strips as Sandwich Grafting", PRS Global Open, Apr. 2017; 5(4):e1301; DOI: 10.1097/GOX.0000000000001301.

Yaqub et al., "The Use of Autogenous Auricular Cartilage in the Management of Upper Eyelid Entropion", Eye (1997) 11:801-805.

Elder et al., "Effects of antigen removal on a porcine osteochondral xenograft for articular cartilage repair", Journal of Biomedical Materials Research Part A, 2018, 106(8), 2251-2260. doi:10.1002/jbm.a.36411.

Xia et al., "Decellularized cartilage as a prospective scaffold for cartilage repair", Materials Science & Engineering C, (2019) 101:588-595.

Caras et al., "Cloning of decay-accelerating factor suggests novel use of splicing to generate two proteins", Nature, Feb. 1987, 325(6104): 545-549.

Purcell et al., "Alternatively spliced RNAs encode several isoforms of CD46 (MCP), a regulator of complement activation", Immunogenetics, 1991, 33(5-6), 335-344.

Shin et al., "Finite Element Biomechanics of Optic Nerve Sheath Traction in Adduction", Journal of Biomechanical Engineering, Oct. 2017, 139(10): 101010. doi: 10.1115/1.4037562.

Shin et al., "Bilaminar Mechanics of the Human Optic Nerve Sheath", Current Eye Research, 2019, 45(7):854-863.

Bowie et al., "Deciphering the message in protein sequences: tolerance to amino acid substitutions", Science, 1990, 247(4948): 1306-1310.

Winkler, "The Effect of Halides (NaCl and Nal) on in Vitro Pancreatic Elastase Activity", Connective Tissue Research, 1978, 6(2): 89-92.

Kafienah et al., "Cleavage of native type I collagen by human neutrophil elastase", Biochemical Journal, 1998, 330(2): 897-902.

Medof et al., "Cloning and characterization of cDNAs encoding the complete sequence of decay-accelerating factor of human complement", Proc. Nat. Acad. Sci. USA, 84: 2007-11 (1987).

Petranka et al., "Structure of the CD59-encoding gene: Further evidence of a relationship to murine lymphocyte antigen Ly-6 protein", Proc. Natl. Acad. Sci. USA, 1992, 89:7876-7879.

Petranka et al., "Structure of the CD59-encoding gene: Further evidence of a relationship to murine lymphocyte antigen Ly-6 protein", Proc. Natl. Acad. Sci. USA, Corrections, 1993, 90:5878.

Chan et al., "Spherical indentation testing of poroelastic relaxations in thin hydrogel layers", Soft Matters, 2012, 8(5):1492-1498.

* cited by examiner

CARTILAGE TREATMENT FOR USE IN EYELID RECONSTRUCTION

CROSS-REFERENCE TO RELATED APPLICATIONS

This application is a National Phase Application of PCT International Application No. PCT/US22/26938, International Filing Date Apr. 29, 2022, which claims benefit of U.S. Provisional Patent Application No. 63/182,278, filed Apr. 30, 2021, which are incorporated herein by reference in their entirety.

FIELD OF INTEREST

The present disclosure relates to methods for preparing ear cartilage for facial and periocular reconstruction, including upper eyelid reconstruction, after trauma, disease, or tumor excision. The present disclosure also relates to compositions, uses, and methods for reconstructing an eyelid. The present disclosure also relates to kits for preparing ear cartilage for eyelid reconstruction. The disclosed compositions, uses, kits, and methods may also be used for autograft, allograft, isograft, and xenograft transplantation, for stored or banked grafts, and for other therapeutic uses.

BACKGROUND

Eyelid reconstructions, including upper eyelid reconstruction, after trauma, disease, or tumor excision can be a challenge when most or all of the eyelid is missing. For example, reconstruction of extensive upper eyelid defects (i.e., greater than 50% of the area of the upper eyelid missing) often depends on contralateral eyelid tarsal free grafts or pedicled flaps, such as reverse Hughes or Cutler-Beard type procedures.

There are currently no xenograft or allograft tarsal substitutes that can safely and routinely be placed in the upper eyelid. Although auricular cartilage is abundant, and may be similar in thickness to native tarsus, the presence of elastin protein makes auricular cartilage rigid, and thus renders the cartilage too stiff to use as a tarsal substitute in the upper or lower eyelid, as such rigidity in the upper or lower eyelid poses an imminent risk of causing corneal damage with blinking. Moreover, unlike nasal septal cartilage, auricular cartilage is not naturally attached to mucosa, thus rendering the surface of the cartilage itself too rough and abrasive to be placed in direct contact with the cornea. Often times such a composite graft is prepared whereby a mucosal lining such as free conjunctiva, nasal cavity mucosa or buccal mucosa is attached to the surface of a cartilage graft before it is placed in contact with the eye surface.

The enzyme elastase is a serine protease enzyme from the class of proteases (peptidases) that break down proteins. Elastase breaks down elastin, an elastic fiber that, together with collagen, determines the mechanical properties of connective tissue, in addition to some antibacterial and antiviral activities. Elastin breakdown is accomplished through the cleavage of peptide bonds in the target proteins, particularly peptide bonds on the carboxyl side of small, hydrophobic amino acids, such as glycine, alanine, and valine. Elastase is inhibited by the acute-phase protein α1-antitrypsin (alpha1-antitrypsin; A1AT), which is secreted by the liver cells into the serum, and which binds almost irreversibly to the active site of elastase and trypsin.

It would be desirable to utilize cartilage, such as elastic cartilage of the ear, as a source for eyelid reconstruction, including upper or lower eyelid reconstruction. Auricular cartilage is too stiff and abrasive on the eye surface to be used routinely for reconstruction of the eyelid. A major gap in treatment exists, wherein there is an inability to provide and use cartilage-based materials and other treatments where most needed in eyelid reconstructions (e.g., upper or lower eyelid reconstruction). It would be desirable to develop a method to soften cartilage for use in eyelid reconstruction, while avoiding cartilage destruction.

SUMMARY

In some aspects, provided herein is a method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips. In some embodiments, washing is provided to remove residual elastase enzyme. In some embodiments, the incubation in a buffered elastase solution and washing steps precede the preparing of the strips.

In some aspects, provided herein is a method of reconstructing an eyelid comprising implanting ear cartilage prepared in accordance with the above method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm, and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips. In some embodiments, washing is provided to remove residual elastase enzyme. In some embodiments, the incubation in a buffered elastase solution and washing steps precede the preparing of the strips.

In some aspects, provided herein is a use of ear cartilage prepared in accordance with the above method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips, for reconstructing an eyelid in a subject in need thereof. In some embodiments, washing is provided to remove residual elastase enzyme. In some embodiments, the incubation in a buffered elastase solution and washing steps precede the preparing of the strips.

In some aspects, provided herein is a composition for reconstructing an eyelid, the composition comprising scaphoid fossa ear cartilage or the conchal bowl ear cartilage cut into strips of about 4-8 mm×about 10-20 mm and about 0.5 mm thick for the upper eyelid, or about 3-6 mm×about 10-20 mm and about 0.5 mm thick for the lower eyelid, following removal of the perichondrium, incubated in a buffered elastase solution, and washed, wherein the instantaneous Young modulus of the strip following washing is between about 100 and about 1000 MPa and equilibrium Young modulus is between about 1 and about 10 MPa. In some embodiments, the incubation in a buffered elastase solution and washing steps precede the cutting into strips.

In some aspects, provided herein is a method for preparing ear cartilage for eyelid reconstruction comprising the steps of: (a) harvesting ear cartilage from the scaphoid fossa or the conchal bowl and removing the perichondrium; (b) incubating the cartilage in a buffered elastase solution; (c) washing the cartilage; and (d) preparing strips of cartilage of about 4-8 mm×about 10-20 mm and about 0.5 mm thick for the upper eyelid, or about 3-6 mm×about 10-20 mm and about 0.5 mm thick for the lower eyelid. In some embodiments, washing is provided to remove residual elastase enzyme. In some embodiments, the cartilage is incubated with an elastase inhibitor after step (b) or (c).

In some aspects, provided herein is a method of reconstructing an eyelid comprising implanting ear cartilage prepared in accordance with the above method for preparing ear cartilage for eyelid reconstruction comprising the steps of: (a) harvesting ear cartilage from the scaphoid fossa or the conchal bowl and removing the perichondrium; (b) incubating the cartilage strips in a buffered elastase solution; (c) washing the cartilage; and (d) preparing strips of cartilage of about 4-8 mm×about 10-20 mm, and about 0.5 mm thick for the upper eyelid, or about 3-6 mm×about 10-20 mm and about 0.5 mm thick for the lower eyelid. In some embodiments, washing is provided to remove residual elastase enzyme. In some embodiments, the cartilage is incubated with an elastase inhibitor after step (b) or (c).

In some aspects, provided herein is a use of ear cartilage prepared in accordance with the above method for preparing ear cartilage for eyelid reconstruction comprising the steps of: (a) harvesting ear cartilage from the scaphoid fossa or the conchal bowl and removing the perichondrium; (b) incubating the cartilage in a buffered elastase solution; (c) washing the cartilage strips; and (d) preparing strips of cartilage of about 4-8 mm×about 10-20 mm and about 0.5 mm thick for the upper eyelid, or about 3-6 mm×about 10-20 mm and about 0.5 mm thick for the lower eyelid, for reconstructing an eyelid in a subject in need thereof. In some embodiments, washing is provided to remove residual elastase enzyme. In some embodiments, the cartilage is incubated with an elastase inhibitor after step (b) or (c).

In some aspects, provided herein is a composition for reconstructing an eyelid, the composition comprising scaphoid fossa ear cartilage or the conchal bowl ear cartilage cut into strips of about 4-8 mm×about 10-20 mm and about 0.5 mm thick for the upper eyelid, or about 3-6 mm×about 10-20 mm and about 0.5 mm thick for the lower eyelid, following removal of the perichondrium, incubated in a buffered elastase solution, and washed, wherein the instantaneous Young modulus of the strip following washing is between about 100 and about 1000 MPa and equilibrium Young modulus is between about 1 and about 10 MPa. In some embodiments, the incubation in a buffered elastase solution and washing steps precede the cutting into strips. In some embodiments, the incubation in elastase solution may precede the cutting into strips. In some embodiments, the cartilage is incubated with an elastase inhibitor, then washed.

In any of the foregoing embodiments wherein the perichondrium is removed, the perichondrium may be removed before or after elastase treatment, or when included, after elastase inhibitor treatment.

In some aspects, provided herein is a kit for reconstructing an eyelid from an ear cartilage, the kit comprising: (a) a buffered elastase solution; (b) a buffered elastase inhibitor solution; and (c) optionally, a buffered wash solution.

In some aspects, disclosed herein is method of treating a disease or medical condition, or of alleviating symptoms thereof, at a focus of interest in a subject in need, said method comprising surgically reconstruction using cartilage prepared as described herein. In some embodiments, the reconstruction is for cosmetic purposes. In some embodiments the reconstruction is for functional purposes. In some embodiments, the cartilage is used for reconstruction of an upper eyelid, a lower eyelid, an ocular surface, a cornea, a sclera, an ear, a nasal septum, a nasal dorsum, a nasal bridge, or a nostril. In some embodiments, the cartilage is used to cover and protect a glaucoma drainage device. The appropriate size of the cartilage strip may be prepared for the particular use. Elastase treatment may precede or follow the trimming of the cartilage to the size for implantation.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
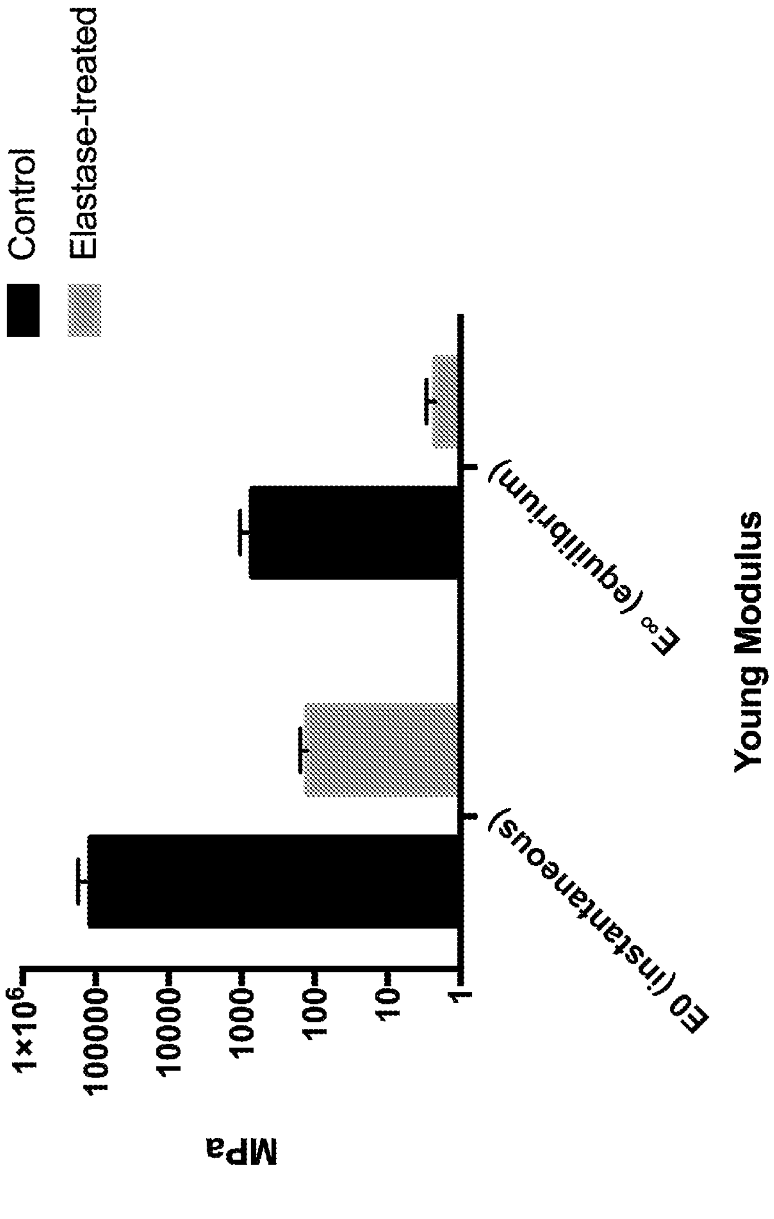
FIG. 1 shows the results of cartilage indentation testing. Compared to control cartilage, elastase treated samples exhibited lower mean (standard deviation) compressive Young modulus, instantaneously [$E_0$] $1.27\times10^2$ ($3.0\times10^2$) vs. $1.18\times10^5$ ($5.58\times10^4$) MPa and at equilibrium [$E_\infty$] $7.19\times10^2$ ($3.4\times10^2$) vs. $2.23\times10^0$ ($7.0\times10^{-1}$) MPa.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

In the following detailed description, numerous specific details are set forth in order to provide a thorough understanding of a method of reconstructing an eyelid comprising implanting ear cartilage, and the uses thereof for treating patients in need of eyelid reconstruction (including upper or lower eyelid reconstruction), such as after trauma, disease, or tumor excision can be a challenge when most or all of the eyelid is missing. However, it will be understood by those skilled in the art that the production of the reconstructed eyelid and uses thereof may be practiced without these specific details. In other instances, well-known methods, procedures, and components have not been described in detail so as not to obscure their description.

It would be desirable to utilize cartilage, such as elastic cartilage of the ear, as a source for eyelid reconstruction, including upper or lower eyelid reconstruction. Reducing the stiffness of ear cartilage is needed to prepare an acceptable eyelid reconstruction. Such reduced stiffness can be achieved by treating the ear cartilage with elastase. However, previous studies have shown that neutrophil-derived, elastase-treated ear cartilage results in cartilage destruction. Thus, there remains an unmet need for elastase-treated cartilage compositions and methods of making and using the same for eyelid reconstructions (e.g., for upper or lower eyelid reconstruction), including, but not limited to, those utilizing elastase-treated ear cartilage. A major gap in treatment exists, wherein there is an inability to provide cartilage-based materials and other treatments where most needed in eyelid reconstructions (e.g., upper or lower eyelid reconstruction), while avoiding cartilage destruction.

Provided herein are compositions comprising elastase-treated cartilage, methods of making the same, and treatments and uses thereof for eyelid reconstruction (e.g., for upper or lower eyelid reconstruction), including in a patient in need thereof. Moreover, such cartilage may also find uses in other reconstructive procedures in which cartilage of reduced stiffness is required or desired, such as, but not limited to, reconstruction of the nose. Such other non-limiting examples include an ocular surface, a cornea, a sclera, an ear, a nasal septum, a nasal dorsum, a nasal bridge, or a nostril. In some embodiments, the cartilage is used to cover and protect a glaucoma drainage device.

Elastase breaks down elastin, an elastic fiber that, together with collagen, determines the mechanical properties of connective tissue. Elastin is usually associated with other proteins in connective tissues. Elastic fiber in humans is a mixture of amorphous elastin and fibrous fibrillin, both of which are primarily made of smaller amino acids such as glycine, valine, alanine, and proline. Collagen is the main structural protein in the extracellular matrix in the various connective tissues in the body and is the most abundant protein in mammals, consisting of amino acids bound together to form a triple helix of elongated fibril known as a collagen helix.

Cartilage, a resilient and smooth elastic tissue, is a structural component of the rib cage, the ear, the nose, the bronchial tubes, the intervertebral discs, and many other body components. It is composed of glycosaminoglycans, proteoglycans, collagen fibers and, in some cases, elastin. Cartilage is composed of specialized cells called chondrocytes that produce a large amount of collagenous extracellular matrix, abundant ground substance that is rich in proteoglycan and elastin fibers. Cartilage is avascular and aneural, obtaining nutrients via diffusion, but has limited repair capabilities. There are three types of cartilage (fibrocartilage, hyaline cartilage, and elastic cartilage), which differ in relative amounts of collagen and proteoglycan.

Fibrocartilage consists of a mixture of white fibrous tissue and cartilaginous tissue in various proportions and is located primarily in the joints. It is the only type of cartilage that contains Type I collagen, in addition to the normal type II. While it owes its elasticity to the latter of these constituents, its inflexibility and toughness are due to the former.

Hyaline cartilage is primarily found on many joint surfaces and in the ribs, nose, larynx, and trachea. It has a firm consistency and contains a considerable amount of collagen. Hyaline cartilage matrix is primarily made of type II collagen and chondroitin sulphate, both of which are also found in elastic cartilage. Hyaline cartilage exists on the ventral ends of ribs, in the larynx, trachea, and bronchi, and on the articulating surfaces of bones. It provides these structures with a definite, but pliable, form. Although the presence of collagen fibers makes such structures and joints strong, it has limited mobility and flexibility.

Elastic cartilage (yellow cartilage) is a type of cartilage present in the outer ear (pinnae, external ear flaps of many mammals), Eustachian tube, and epiglottis (part of the larynx). It contains elastic fiber networks and collagen type II fibers and comprises many yellow elastic fibers lying in a solid matrix. These fibers form bundles and provide elastic cartilage with great flexibility to enable it to withstand repeated bending. Between the fibers lie chondrocytes. The principal protein of elastic cartilage is elastin.

In some aspects, disclosed herein is a method for preparing ear cartilage for eyelid reconstruction comprising the steps of: (a) harvesting ear cartilage from the scaphoid fossa or the conchal bowl and removing the perichondrium; (b) preparing strips of cartilage for the upper eyelid or for the lower eyelid; (c) incubating the cartilage strips in a buffered elastase solution; and (d) washing the cartilage strips.

In some aspects, disclosed herein is a method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips. As noted elsewhere herein, the elastase treatment may be performed before or after the cartilage is prepared into strips. In other embodiments, after elastase treatment, the cartilage or cartilage strips may be incubated with an elastase inhibitor. In some embodiments the cartilage or cartilage strips may be rinsed or washed between or after one or more of the steps.

In any of the foregoing embodiments wherein the perichondrium is removed, the perichondrium may be removed before or after elastase treatment, or when included, after elastase inhibitor treatment.

In some embodiments, the ear cartilage is an autograft, allograft, isograft, or xenograft.

In some embodiments, the ear cartilage is cadaveric.

In some embodiments, the elastase is porcine pancreatic elastase. In some embodiments, the elastase is bacteria derived. In some embodiments, the elastase is human elastase. In some embodiments the elastase is human pancreatic elastase. In some embodiments the elastase is human neutrophil elastase. In humans, eight elastase genes have been classified into four groups: (1) five chymotrypsin-like elastase family (CELA) members (member 1 [CELA1], member 2A [CELA2A], member 2B [CELA2B], member 3A [CELA3A], and member 3B [CELA3B]); (2) one chymotrypsin family member (chymotrypsin C [CTRC]); (3) one neutrophil family member (neutrophil elastase [ELANE]); and (4) one macrophage family member (macrophage metalloelastase [MMP12]).

In some embodiments, soybean trypsin inhibitor or another enzymatic inhibitor or a small molecule inhibitor may be included with the elastase solution to mitigate non-specific enzymatic digestion by elastase. See, for example, Kafienah et al., 1998, Biochem. J 339 (Pt 2):897-902.

In some embodiments, the elastase activity is equivalent to about 10 units/milliliter (U/mL) of buffer.

In some embodiments, the buffer is at about pH 6.5 to about pH 9.5. In some embodiments, the incubating is from about 30 minutes to about 24 hours.

In some embodiments, the incubating is at a temperature of about 25 degrees Celsius (deg. C) to about 37 deg. C (about 25° C. to about 37° C.).

In some embodiments, the washing comprises an elastase inhibitor. In some embodiments, the washing comprises multiple rinses, e.g., in sterile buffer. In some embodiments, the elastase is porcine pancreatic elastase, and the washing comprises rinsing until the detectability of porcine antigens is below a minimum detectable level, see, for example, Elder et al., 2018, J Biomed Mater Res A 106(8):2251-2260.

In some embodiments, the method further comprises testing the tensile force of the strips following washing. In some embodiments, the instantaneous Young modulus of the strip following washing is between about 100-1000 MPa, such as between about 100 and 500 MPa, and the equilibrium Young modulus of the strip following washing is between about 1 and 10 MPa, such as between about 1 and 5 MPa. In some embodiments, the abrasiveness of the ear cartilage to be used as a replacement eyelid is examined prior to implanting of the treated cartilage on the recipient's eye. In some embodiments, the replacement eyelid is examined following implanting of the treated cartilage on the recipient's eye. In some embodiments, the abrasiveness testing is performed under aseptic conditions. In some embodiments, when the ear cartilage is an allograft or xenograft, the cartilage is decellularized prior to incubating step (c).

In some embodiments, all steps are performed under aseptic conditions.

In some embodiments, the ear cartilage is from a donor not having a connective tissue disease.

In some aspects, provided herein is a method of reconstructing an eyelid comprising implanting ear cartilage prepared in accordance with the above method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips. As noted elsewhere herein, the size of the cartilage strips may be modified for reconstruction or use for other purposes.

In some aspects, provided herein is a use of ear cartilage prepared in accordance with the above method for preparing ear cartilage for eyelid reconstruction comprising the steps of: (a) harvesting ear cartilage from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips, for reconstructing an eyelid in a subject in need thereof.

In some aspects, provided herein is a composition for reconstructing an eyelid, the composition comprising scaphoid fossa ear cartilage or conchal bowl ear cartilage cut into strips of about 4-8 mm×about 10-20 mm and about 0.5 mm thick for the upper eyelid, or about 3-6 mm×about 10-20 mm and about 0.5 mm thick for the lower eyelid, following removal of the majority of the perichondrium, incubated in a buffered elastase solution, and washed, wherein the instantaneous Young modulus of the strip following washing is between about 100 and 1000 MPa, for example between about 100 and 500 MPa and equilibrium Young modulus between about 1 and 10 MPa, for example between about 1 and 5 MPa. In some embodiments, after the incubation in a buffered elastase solution, the cartilage is incubated or washed in an elastase inhibitor solution.

In any of the foregoing embodiments wherein the perichondrium is removed, the perichondrium may be removed before or after elastase treatment, or when included, after elastase inhibitor treatment.

In some aspects, provided herein is a kit for reconstructing an eyelid from an ear cartilage, the kit comprising: (a) a buffered elastase solution; (b) an elastase inhibitor solution; and (c) optionally, a buffered wash solution.

In some embodiments, after ear cartilage is harvested from a patient, it is treated with this process and then re-implanted at a different site. For instance, in a patient with an upper or lower eyelid missing after a trauma, a disease, or a tumor excision, ear cartilage is harvested, treated with elastase according to the methods described herein (including proprietary solutions containing elastase in proportions delineated in this process), and re-implanted in the eyelid for reconstruction.

In some embodiments, ear cartilage is harvested from a living donor, treated with elastase according to the methods described herein, and implanted in the eyelid of a recipient patient in need thereof (e.g., in a recipient patient with an upper or lower eyelid missing after a trauma, disease, or tumor excision).

In some embodiments, cadaveric ear cartilage is sterilized and then treated with elastase (in order to soften it to a pre-determined stiffness) and provided as an eyelid tarsus allograft.

In some embodiments, ear cartilage is harvested from a non-human organism (including, but not limited to, a non-human mammal), treated with elastase according to the methods described herein, and implanted in the eyelid of a recipient patient in need thereof (e.g., in a recipient patient with an upper or lower eyelid missing after a trauma, disease, or tumor excision).

As noted herein, use of the methods described herein in preparing ear cartilage suitable for use in eyelid reconstruction also provides for preparing cartilage of any bodily source for use in a location desirous of a cartilage of lower stiffness (e.g., decreased elasticity or increased stretchiness). Thus, the teachings of the disclosure with regard to ear derived cartilage for use in eyelid reconstruction is equally applicable to cartilage from other parts of the body and used in locations where lower stiffness is desired. Non-limiting examples include reconstruction of the nose (e.g., the bridge of the nose, nostril, or septum). Other examples include use in any facial reconstruction, not limited to cosmetic or functional. In one embodiment, the cartilage obtained from the ear is used for reconstruction of the ear.

Ear Cartilage

Disclosed herein are ear cartilage-derived preparations that can be implanted in or grafted to, for example, vertebrate subjects. More particularly, disclosed herein are methods of producing a modified ear cartilage-derived preparation having altered stretchiness (i.e., decreased elasticity and/or increased stretchiness) relative to the corresponding unmodified ear cartilage, without substantially compromising the associated structural or functional integrity of the tissue. Additionally, disclosed herein are methods of producing a group of modified ear cartilage-derived preparations from a group of ear cartilage samples, wherein the stretchiness of tissues in the group of modified ear cartilage-derived preparations has less variation than the stretchiness of tissues in the group of ear cartilage samples, i.e., wherein the percent extension of tissues in the group of modified ear cartilage-derived preparations under a specific amount of tensile force displays less variation than the percent extension of tissues in the group of ear cartilage samples under the same amount of tensile force.

As used herein, "cartilage," a resilient and smooth elastic tissue, is a structural component of the rib cage, the ear, the nose, the bronchial tubes, the intervertebral discs, and many other body components. It is composed of glycosaminoglycans, proteoglycans, collagen fibers and, in some cases, elastin. Cartilage is composed of chondrocyte cells that produce a large amount of collagenous extracellular matrix, an abundant ground substance that is rich in proteoglycan and elastin fibers. Cartilage is avascular and aneural. There are three types of cartilage (fibrocartilage, hyaline cartilage, and elastic cartilage), which differ in relative amounts of collagen and proteoglycan.

"Fibrocartilage" consists of a mixture of white fibrous tissue and cartilaginous tissue in various proportions and is located primarily in the joints. It is the only type of cartilage that contains Type I collagen, in addition to the normal type II.

"Hyaline cartilage" is primarily found on many joint surfaces and in the ribs, nose, larynx, and trachea. It has a firm consistency and contains a considerable amount of collagen. Hyaline cartilage matrix is primarily made of type II collagen and chondroitin sulphate, both of which are also found in elastic cartilage. Hyaline cartilage exists on the ventral ends of ribs, in the larynx, trachea, and bronchi, and on the articulating surfaces of bones. It provides these structures with a definite, but pliable, form.

"Elastic cartilage" ("yellow cartilage") is a type of cartilage present in the outer ear (pinnae, external ear flaps of many mammals), Eustachian tube, and epiglottis (part of the larynx). It contains elastic fiber networks and collagen type II fibers and comprises many yellow elastic fibers lying in a solid matrix. These fibers form bundles and provide elastic cartilage with great flexibility to enable it to withstand repeated bending. Between the fibers lie chondrocytes. The principal protein of elastic cartilage is elastin.

"Ear cartilage" refers to cartilage from the ear.

The "ear" is the organ of hearing and, in mammals, balance. In mammals, the ear typically has three parts—the outer ear, the middle ear, and the inner ear. The outer ear consists of the pinna and the ear canal and is the only visible portion of the ear in most animals. The middle ear includes the tympanic cavity and the three ossicles. The inner ear sits in the bony labyrinth, and contains structures including: the semicircular canals, which enable balance and eye tracking when moving; the utricle and saccule, which enable balance when stationary; and the cochlea, which enables hearing. The ears of vertebrates are placed somewhat symmetrically on either side of the head, an arrangement that aids sound localization.

The "outer ear" ("auris externa", "external ear") is the external portion of the ear and includes the fleshy visible pinna (also called the auricle), the ear canal, and the outer layer of the eardrum (also called the tympanic membrane). The "pinna" or "auricle" consists of the helix (curving outer rim) and the antihelix (inner curved rim) and opens into the ear canal. It consists of a single piece of elastic cartilage with a complicated relief on its inner surface and a fairly smooth configuration on its posterior surface. It is composed of a thin plate of yellow elastic cartilage, covered with integument, and connected to the surrounding parts by ligaments and muscles, and to the commencement of the ear canal by fibrous tissue. "Auricular cartilage" refers to the cartilage of the ear's auricle, the outermost portion of the ear. This cartilage helps maintain the shape of the ear while allowing for flexibility. The tragus protrudes and partially obscures the ear canal, as does the facing antitragus. The hollow region in front of the ear canal is the concha. The ear canal stretches for about 1 inch (2.5 cm). The first part of the canal is surrounded by cartilage, while the second part near the eardrum is surrounded by bone. The skin surrounding the ear canal contains ceruminous and sebaceous glands that produce protective ear wax. The ear canal ends at the external surface of the eardrum.

In one embodiment, ear cartilage is isolated from the scaphoid fossa and the perichondrium is removed as completely as possible without damaging the cartilage. As noted herein, wherein the perichondrium is removed, the perichondrium may be removed before or after elastase treatment, or when included, after elastase inhibitor treatment.

The "scaphoid fossa" or "scapha" is the groove between the helix and the crura of the antihelix.

In one embodiment, the cartilage is harvested from the conchal bowl, which is comprised of the concha cavum and the concha cymba, the region of the ear posterior to the external auditory meatus, and the perichondrium is removed.

The "conchal bowl" or "concha" is the deepest depression in the external ear, which leads directly to the external auditory canal, or external acoustic meatus.

The "acoustic meatus," "auditory meatus," or "auditory canal" is comprised of two passages in the ear; the "external acoustic meatus" leads from the auricle to the tympanic membrane (eardrum) and the internal acoustic meatus is for passage of nerves and blood vessels from the inner ear to the central nervous system.

The "perichondrium" is a dense layer of fibrous connective tissue that covers cartilage in various parts of the body, including the elastic cartilage in parts of the ear, as well as the hyaline cartilage in the trachea and larynx, the nose, the epiglottis, the area where the ribs connect to the sternum, and the area between the spinal vertebrae. It is comprised of an outer fibrous layer (a dense layer of connective tissue containing fibroblasts that produce collagen) and an inner chondrogenic layer (containing fibroblasts that produce chondroblasts and chondrocytes [cartilage cells]).

Removal of the perichondrium can be performed by methods known in the art. In a non-limiting example, the perichondrium is removed as described below. In any of the embodiments herein wherein the perichondrium is removed, the perichondrium may be removed before or after elastase treatment, or when included, after elastase inhibitor treatment.

Harvesting of the ear cartilage comprises a series of steps. In one embodiment, a cutaneous incision is fashioned in the posterior or anterior ear skin overlying either the conchal bowl or the scapha. A number 15 blade is used to incise the perichondrium, and a periosteal elevator is used to separate the cartilage from the perichondrium using blunt dissection. An incision through the cartilage is fashioned, and this is propagated beneath the perichondrium of the opposing side. A periosteal elevator is used to separate the cartilage from the perichondrium of the opposite side using blunt dissection. The cartilage is thus separated (as much as possible without damaging the cartilage) from the periochondrium of both surfaces of the ear.

To facilitate removal of elastin during elastase treatment, the ear cartilage may be cut into smaller pieces in order to increase surface area. Alternatively, it may be cut in order to shape the material prior to treatment and subsequent grafting. In one embodiment, the cartilage strip is cut to be a size needed to approximate the eyelid tarsus that is missing. In one embodiment, the ear cartilage is sized for an upper eyelid into strips of about 4-8 mm wide by about 10-20 mm long and about 0.5 mm thickness. In another embodiment, the ear cartilage is sized for a lower eyelid into strips of about 4-6 mm wide×10-20 mm long and 0.5 mm thick. In one embodiment, the cartilage strip is cut to a size needed for the machine used for tensile strength testing. In one non-limiting example, the ear cartilage is cut into strips of about 2 mm×about 6 mm and about 0.5 mm thickness, e.g., for purposes of tensile strength testing as described herein (e.g., on a horizontally mounted microtensile load cell incorporating a linear motor (IBEX™ Engineering, Newbury Park, CA) and a strain gauge (LSB200, FUTEK™, Irvine, CA)). In another non-limiting example, the ear cartilage is cut into strips of about 4-8 mm wide×about 10-20 mm long and about 0.4 mm thickness, or about 3-6 mm×about 10-20 mm and about 0.5 mm thick, e.g., for purposes of tensile strength testing as described herein (e.g., on a horizontally mounted microtensile load cell incorporating a linear motor (IBEX™ Engineering, Newbury Park, CA) and a strain gauge (LSB200, FUTEK™, Irvine, CA)). In another non-limiting example, the ear cartilage is cut into strips of about 4-6 mm wide×about 10-20 mm long and about 0.4 mm thickness, or about 3-6 mm×about 10-20 mm and about 0.5 mm thick, e.g., for purposes of tensile strength testing as described herein (e.g., on a horizontally mounted microtensile load cell incorporating a linear motor (IBEX™ Engineering, Newbury Park, CA) and a strain gauge (LSB200, FUTEK™, Irvine, CA)). The dimensions may be measured, e.g., thickness using a high precision electronic caliper.

As used herein, the "extracellular matrix" (ECM) is a three-dimensional network of extracellular macromolecules, such as collagen, enzymes, and glycoproteins, that provide structural and biochemical support to surrounding cells. Because multicellularity evolved independently in different multicellular lineages, the composition of ECM varies between multicellular structures; however, cell adhesion, cell-to-cell communication and differentiation are common functions of the ECM. In animals, the ECM includes the interstitial matrix and the basement membrane. "Interstitial matrix" is present between various animal cells (i.e., in the intercellular spaces). Gels of polysaccharides and fibrous proteins fill the interstitial space and act as a compression buffer against the stress placed on the ECM. "Basement membranes" comprise sheet-like depositions of ECM on which various epithelial cells rest. Each type of connective tissue in animals has a type of ECM. For example, collagen fibers and bone mineral comprise the ECM of bone tissue; reticular fibers and ground substance comprise the ECM of loose connective tissue; and blood plasma is the ECM of blood. Components of the ECM are produced intracellularly by resident cells and secreted into the ECM via exocytosis. Once secreted, they then aggregate with the existing matrix.

The ECM is composed of an interlocking mesh of fibrous proteins and glycosaminoglycans (GAGs). "Glycosaminoglycans" (GAGs) are carbohydrate polymers and mostly attached to extracellular matrix proteins to form proteoglycans (hyaluronic acid is a notable exception). Proteoglycans have a net negative charge that attracts positively charged sodium ions (Na+), which attracts water molecules via osmosis, keeping the ECM and resident cells hydrated. Proteoglycans may also help to trap and store growth factors within the ECM. Different types of proteoglycan are found in the ECM. For example, heparan sulfate (HS) is a linear polysaccharide found in all animal tissues, including cartilage. Chondroitin sulfates contribute to the tensile strength of cartilage, tendons, ligaments, and walls of the aorta. Keratan sulfates are present in the cornea, cartilage, bones, and the horns of animals. A non-proteoglycan polysaccharide, hyaluronic acid (or hyaluronan) is a polysaccharide consisting of alternating residues of D-glucuronic acid and N-acetylglucosamine. Hyaluronic acid in the extracellular space confers upon tissues the ability to resist compression by providing a counteracting turgor (swelling) force by absorbing significant amounts of water and is found in abundance in the ECM of load-bearing joints. It is also a chief component of the interstitial gel. Deoxyribonucleic acid (DNA), ribonucleic acid (RNA), and matrix-bound nanovesicles (MBVs) have also been observed within ECM bioscaffolds.

The most common ECM proteins include, e.g., collagens and elastin. Collagens are the most abundant protein in the ECM and in the human body as a whole. Elastins, in contrast to collagens, give elasticity to tissues, allowing them to stretch when needed and then return to their original state. The ECM can exist in varying degrees of stiffness and elasticity, from soft brain tissues to hard bone tissues. The elasticity of the ECM can differ by several orders of magnitude. This property is primarily dependent on collagen and elastin concentrations and plays an influential role in regulating numerous cell functions.

Fibronectins are glycoproteins that connect cells with collagen fibers in the ECM, allowing cells to move through the ECM. Fibronectins bind collagen and cell-surface integrins, causing a reorganization of the cell's cytoskeleton to facilitate cell movement. Laminins are proteins found in the basal laminae of virtually all animals. Rather than forming collagen-like fibers, laminins form networks of web-like structures that resist tensile forces in the basal lamina. They also assist in cell adhesion. Laminins bind other ECM components such as collagens and nidogens.

As used herein, "decellularization" is a process used in biomedical engineering to isolate the extracellular matrix (ECM) of a tissue from its inhabiting cells, leaving an ECM scaffold of the original tissue, which can be used in artificial organ and tissue regeneration. Organ and tissue transplantation treat a variety of medical problems, ranging from end organ failure to cosmetic surgery. One of the greatest limitations to organ transplantation derives from organ rejection caused by antibodies of the transplant recipient reacting to donor antigens on cell surfaces within the donor organ. Because of unfavorable immune responses, transplant patients suffer a lifetime taking immunosuppressing medication. In contrast, the decellularization process creates a natural biomaterial to act as a scaffold for cell growth, differentiation, and tissue development. By recellularizing an ECM scaffold with a patient's own cells, the adverse immune response is eliminated.

With a wide variety of decellularization-inducing treatments are available in the art, combinations of physical, chemical, and enzymatic treatments are carefully monitored to ensure that the ECM scaffold maintains the structural and chemical integrity of the original tissue. The acquired ECM scaffold can be used to reproduce a functional organ (e.g., eyelid), e.g., by introducing progenitor cells, or adult stem cells (ASCs), and allowing them to differentiate within the scaffold to develop into the desired tissue. In some embodiments, the progenitor cells or ASCs are derived from the recipient to avoid rejection of the graft. The produced organ or tissue can be transplanted into a recipient. In contrast to cell surface antibodies, which are removed during decellularization, the biochemical components of the ECM are conserved between hosts, so the risk of a hostile immune response is minimized. Proper conservation of ECM fibers, growth factors, and other proteins is imperative to the progenitor cells differentiating into the proper adult cells.

Methods of decellularization include, e.g., physical, chemical, and enzymatic treatments.

"Physical decellularization" methods are used to lyse, kill, and remove cells from the matrix of a tissue through the use of temperature, force and pressure, and electrical disruption. Temperature methods are often used in a rapid freeze-thaw mechanism, which causes microscopic ice crystals form around the plasma membrane (during freezing) and cell lysis (upon thawing). After lysing the cells, the tissue can be further exposed to liquidized chemicals that degrade and wash out the undesirable components. Temperature methods conserve the physical structure of the ECM scaffold, but are best for thick, strong tissues. Pressure decellularization involves the controlled use of hydrostatic pressure applied to a tissue or organ, optimally at high temperatures to avoid unmonitored ice crystal formation that could damage the scaffold. Electrical disruption of the plasma membrane is another option to lyse the cells housed in a tissue or organ. By exposing a tissue to electrical pulses, micropores are formed at the plasma membrane. The cells eventually die after their homeostatic electrical balance is ruined through the applied stimulus. This electrical process is called "non-thermal irreversible electroporation" (NTIRE) and is limited to small tissues and the limited possibilities of inducing an electric current in vivo.

"Chemical decellularization" involves selecting a combination of chemicals depending on the thickness, extracellular matrix composition, and intended use of the tissue or organ. Chemicals used to kill and remove the cells include, e.g., acids, alkaline treatments, ionic detergents, non-ionic detergents, and zwitterionic detergents. When collagen is not present in a high concentration or when it is not needed in the tissue, enzymes may be a viable option for decellularization.

In some embodiments, detergents are used for chemical decellularization. Detergents act effectively to lyse the cell membrane and expose the contents to further degradation. Detergents may be ionic or non-ionic.

In a non-limiting example, the ionic detergent comprises sodium dodecyl sulfate (SDS), which has a high efficacy for lysing cells without significant damage to the ECM, although it may slightly disrupt the ECM structure. After SDS lyses the cell membrane, endonucleases and exonucleases degrade the genetic contents, while other components of the cell are solubilized and washed out of the matrix. Alkaline and acid treatments can be effective companions with an SDS treatment due to their ability to degrade nucleic acids and solubilize cytoplasmic inclusions.

In a non-limiting example, the non-ionic detergent comprises 2-[4-(2,4,4-trimethylpentan-2-yl)phenoxy]ethanol (Triton X-100), which is popular because of its ability to disrupt the interactions between lipids and between lipids and proteins. Triton X-100 does not disrupt protein-protein interactions, which is beneficial to keeping the ECM intact.

Ethylenediamine tetra-acetic acid (EDTA) is a chelating agent that binds calcium, which is a necessary component for proteins to interact with one another. By making calcium unavailable, EDTA prevents the integral proteins between cells from binding to one another. EDTA is often used with trypsin, an enzyme that acts as a protease to cleave the already existing bonds between integral proteins of neighboring cells within a tissue. The EDTA-Trypsin combination may be used for decellularizing tissues.

"Enzyme decellularization" treatments are used to break the bonds and interactions between nucleic acids, interacting cells through neighboring proteins, and other cellular components. Lipases, thermolysin, galactosidase, nucleases, and trypsin have all been used in the removal of cells. After a cell is lysed with a detergent, acid, physical pressure, etc., endonucleases and exonucleases can begin the degradation of the genetic material. Endonucleases cleave DNA and RNA in the middle of sequences. Benzoase, an endonuclease, produces multiple small nuclear fragments that can be further degraded and removed from the ECM scaffold. Exonucleases act at the end of DNA sequences to cleave the phosphodiester bonds and further degrade the nucleic acid sequences. Enzymes such as trypsin act as proteases that cleave the interactions between proteins. While trypsin can have adverse effects on collagen and elastin fibers of the ECM, using it in a time-sensitive manner controls any potential damage it could cause on the extracellular fibers. Dispase is used to prevent undesired aggregation of cells, which is beneficial in promoting their separating from the ECM scaffold. Experimentation has shown dispase to be most effective on the surface of a thin tissue. To successfully remove deep cells of a tissue with dispase, mechanical agitation is often included in the process. Generally, collagenase is only used when the ECM scaffold product does not require an intact collagen structure. Lipases are commonly used when decellularized skin grafts are needed. Lipase acids function in decellularizing dermal tissues through delipidation and cleaving the interactions between heavily lipidized cells. The enzyme, α-galactosidase (alpha-galactosidase) is a relevant treatment when removing the Gal epitope antigen from cell surfaces.

In some embodiments, e.g., when the ear cartilage is an allograft or xenograft, the cartilage is decellularized prior to treatment with elastase. Decellularization may take place before or after excising or cutting of the ear cartilage or otherwise reducing the ear cartilage, or a component or portion thereof, into smaller pieces (e.g., strips). In some embodiments, decellularization takes place after cutting of the ear cartilage or component or portion thereof into smaller pieces (e.g., strips). See for example Xia et al., 2019, Mater Sci Eng C Mater Biol Appl 101:588-595.

As used herein, an "acellular ear cartilage" comprises an ear-cartilage-derived structure that is made from any of a wide range of collagen-containing tissues by removing all, or substantially all, viable cells and all detectable subcellular components and/or debris generated by killing cells. In some embodiments, an acellular ear cartilage comprises an ear-cartilage-derived structure that has undergone decellularization.

As used herein, an acellular ear cartilage lacking "substantially all viable cells" is an acellular ear cartilage in which the concentration of viable cells is less than 1% (e.g., less than: 0.1%; 0.01%; 0.001%; 0.0001%; 0.00001%; or 0.000001%) of that in the tissue or organ from which the acellular ear cartilage was made. As used herein, a "modified acellular ear cartilage" is an acellular ear cartilage that has been subjected to elastase treatment, e.g., as described herein. Except where otherwise explicitly noted, the various statements herein regarding the use, characteristics, etc. of acellular ear cartilages apply equally to modified acellular ear cartilages. The acellular ear cartilage of the present disclosure may lack a basement membrane.

Biological functions retained by acellular ear cartilage include cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such glycosaminoglycans (e.g., hyaluronan) or proteoglycans, or other adhesins). Structural functions retained by useful acellular matrices include maintenance of histological architecture, maintenance of the three-dimensional array of the tissue's components and physical characteristics such as strength, elasticity, and durability, defined porosity, and retention of macromolecules. The efficiency of the biological functions of an acellular ear cartilage can be measured, for example, by the ability of the acellular ear cartilage to support cell proliferation and is at least 50% (e.g., at least: 50%; 60%; 70%; 80%; 90%; 95%; 98%; 99%; 99.5%; 100%; or more than 100%) of that of the ear cartilage from which the acellular ear cartilage is made.

Furthermore, while an acellular ear cartilage may have been made from one or more individuals of the same species as the recipient of the acellular ear cartilage graft, this is not necessarily the case. Thus, for example, an acellular ear cartilage can have been made, e.g., from a porcine tissue and be implanted, e.g., in a human patient. Species that can serve as recipients of acellular ear cartilage and donors of tissues or organs for the production of the acellular ear cartilage include, without limitation, humans, non-human primates (e.g., monkeys, baboons, or chimpanzees), porcine, bovine, horses, goats, sheep, dogs, cats, rabbits, guinea pigs, gerbils, hamsters, rats, or mice. For instance, donors may be animals (e.g., pigs) that have been genetically engineered to lack the terminal galactose-α-1,3 galactose (galactose-alpha-1,3 galactose) moiety. For descriptions of appropriate animals see co-pending U.S. application Ser. No. 10/896,594 and U.S. Pat. No. 6,166,288, the disclosures of all of which are incorporated herein by reference in their entirety. Additionally, species that can serve as recipients of acellular ear cartilage and donors of tissues or organs for the production of the acellular ear cartilage include, without limitation, a nonhuman transgenic animal, including a nonhuman transgenic animal useful in xenotransplantation with reduced rejection (e.g., comprising an artificially introduced nucleic acid that expresses at least one enzyme functional in said animal which masks or reduces the level of a xenoreactive antigen (e.g., a fucosyltransferase [e.g., alpha-(1,2)fucosyltransferase], a sialyltransferase [e.g., alpha-(2,6)sialyltransferase], a acetylglucosaminyltransferase [e.g., beta-(1,3) N-acetylglucosaminyltransferase] or other suitable glycosyltransferase that will mask or reduce the level of the xenoreactive antigens, such as antigenic gal epitope) or a nucleic acid that expresses at least one complement inhibitor functional in a recipient species or individual (e.g., CD59 glycoprotein [MAC-inhibitory protein (MAC-IP), membrane inhibitor of reactive lysis (MIRL), or protectin], complement decay-accelerating factor [DAF or CD55], and/or monocyte chemoattractant protein [MCP] or other complement inhibitors with respect to humans in general or a specific human individual), said animal being a source of an organ, tissue, or cell for xenotransplantation, and anatomically and physiologically compatible with the recipient species or individual. Other examples of complement inhibitors include, but are not limited to, Factor I, Factor H, C4 binding protein (C4 bp), CR1, CR2, C8 binding protein (C8 bp), homologous restriction factor (HRF), macrophage inflammatory protein (MIP), P-18, HRF-20, and membrane inhibitor of reactive lysis (MIRL). The structure of the CD59 gene is described in Petranka et al., Proc. Nat. Acad. Sci. (USA) 89:7876-79 (1992) and 90:5878 (1993) (correction), as well as PCT Application WO 96/12804. For DAF sequences, see Medof et al., Proc. Nat. Acad. Sci. USA, 84: 2007-11 (1987); Caras et al., Nature, 325: 545-9 (1987), and recombinant human CD55/DAF is commercially available (#2009-CD; R&D SYSTEMS™). For MCP sequences, see Purcell et al., Immunogenetics, 33: 335-344 (1991). Recombinant or other species include, but are not limited to, a vertebrate animal, i.e., a mammal, bird, reptile, fish, or amphibian. Among mammals, non-limiting examples are human or non-human primates (e.g., chimpanzee, African green monkey). Also among mammals, non-limiting examples of animals belong to the order Artidactyla (e.g., cows, pigs, sheep, goats, horses), Rodentia (e.g., mice, rats), Lagomorpha (e.g., rabbits), or Carnivora (e.g., cats, dogs). Should other animals be considered for use in the method of the present invention, among birds, non-limiting examples include the orders Anseriformes (e.g., ducks, geese, swans) or Galliformes (e.g., quails, grouse, pheasants, turkeys, and chickens), and among fish, non-limiting examples include the order Clupeiformes (e.g., sardines, shad, anchovies, whitefish, salmon, and trout).

As used herein, "cryopreservation" or "cryoconservation" comprises a process by which organelles, cells, tissues, extracellular matrix, organs, or any other biological constructs susceptible to damage caused by unregulated chemical kinetics are preserved by cooling to very low temperatures (e.g., −80° C. using solid carbon dioxide or −196° C. using liquid nitrogen). At sufficiently low temperatures, enzymatic or chemical activity which might cause damage to the biological material in question is effectively stopped. Cryopreservation methods seek to reach low temperatures without causing additional damage caused by the formation of ice crystals during freezing. In non-limiting examples, cryopreservation comprising coating the material to be frozen with a class of molecules termed "cryoprotectants."

In some embodiments, ear cartilage or acellular ear cartilage is cryopreserved prior to undergoing elastase treatment. In some embodiments, the acellular ear cartilage is cryopreserved after decellularization and prior to undergoing elastase treatment. The ear cartilage or acellular ear cartilage is incubated in a cryopreservation solution. This solution generally contains one or more cryoprotectants to minimize ice crystal damage to the structural matrix that could occur during freezing. If the tissue is to be freeze dried, the solution will generally also contain one or more dry-protective components, to minimize structural damage during drying, which may include a combination of an organic solvent and water which undergoes neither expansion nor contraction during freezing. The cryoprotective and dry-protective agents can be the same one or more substances. If the ear cartilage or acellular ear cartilage is not going to be freeze dried, it can be frozen by placing it (in a sterilized container) in a freezer at about −80° C., or by plunging it into sterile liquid nitrogen, and then storing at a temperature below −160° C. until use. The sample can be thawed prior to use by, for example, immersing a sterile non-permeable vessel (see below) containing a water bath at about 37° C. or by allowing the tissue to come to room temperature under ambient conditions.

In some embodiments, the ear cartilage or acellular ear cartilage can be cryopreserved after undergoing elastase treatment, e.g., according to the methods above.

If the ear cartilage or acellular ear cartilage is to be frozen and freeze dried, following incubation in the cryopreservation solution, it is packaged inside a sterile vessel that is permeable to water vapor, yet impermeable to bacteria, e.g., a water vapor permeable pouch or glass vial. In a non-limiting example, one side of a suitable pouch consists of medical grade porous TYVEK™ membrane, a trademarked product of DUPONT™ of Wilmington, Del. This membrane is porous to water vapor and impervious to bacteria and dust. The TYVEK™ membrane is heat sealed to an impermeable polyethylene laminate sheet, leaving one side open, thus forming a two-sided pouch. The open pouch is sterilized by irradiation (e.g., γ-irradiation, gamma-irradiation) prior to use. The ear cartilage or acellular ear cartilage is aseptically placed (through the open side) into the sterile pouch. The open side is then aseptically heat sealed to close the pouch. The packaged ear cartilage or acellular ear cartilage is henceforth protected from microbial contamination throughout subsequent processing steps.

The vessel containing the tissue is cooled to a low temperature at a specified rate that is compatible with the specific cryoprotectant formulation to minimize the freezing damage. See, e.g., U.S. Pat. No. 5,336,616 for examples of appropriate cooling protocols. The tissue is then dried at a low temperature under vacuum conditions, such that water vapor is removed sequentially from each ice crystal phase.

At the completion of the drying of the samples in the water vapor permeable vessel, the vacuum of the freeze-drying apparatus is reversed with a dry inert gas such as nitrogen, helium, or argon. While being maintained in the same gaseous environment, the semipermeable vessel is placed inside an impervious (i.e., impermeable to water vapor as well as microorganisms) vessel (e.g., a pouch), which is further sealed, e.g., by heat and/or pressure. Where the ear cartilage or acellular ear cartilage sample was frozen and dried in a glass vial, the vial is sealed under vacuum with an appropriate inert stopper, and the vacuum of the drying apparatus is reversed with an inert gas prior to unloading. In either case, the final product is hermetically sealed in an inert gaseous atmosphere. The freeze-dried ear cartilage or acellular ear cartilage may be stored under refrigerated conditions until treated with elastase.

After rehydration of elastase-treated ear cartilage or acellular ear cartilage, as described below, histocompatible, viable cells can be restored to the ear cartilage or acellular ear cartilage to produce a permanently accepted graft that may be remodeled by the host. This is generally done just prior to placing the ear cartilage or acellular ear cartilage in a mammalian subject (e.g., in place of the eyelid [tarsus, either upper or lower] between the conjunctiva and the orbicularis oculi muscle). Where the matrix has been freeze-dried, it will be done after rehydration. In one embodiment, histocompatible viable cells may be added to the matrices by standard in vitro cell culturing techniques prior to transplantation, or by in vivo repopulation following transplantation. In vivo repopulation can be by the recipient's own cells migrating into the ear cartilage or acellular ear cartilage or by infusing or injecting cells obtained from the recipient or histocompatible cells from another donor into the ear cartilage or acellular ear cartilage in situ.

The cell types used for reconstitution will be compatible with the new role of the eyelid (e.g., the upper or lower eyelid) to which the ear cartilage or acellular ear cartilage is being remodeled. For example, the primary requirement for reconstitution of an eyelid with an ear cartilage or acellular ear cartilage is the restoration of the structural properties of the eyelid tarsus (e.g., the structural collagen network that supports the upper or lower eyelid). For example, cells derived directly from the intended recipient can be used to reconstitute an ear cartilage or acellular ear cartilage, and the resulting composition can be grafted to the recipient in the form of a meshed split-skin graft. Alternatively, cultured (autologous or allogeneic) cells can be added to the ear cartilage or acellular ear cartilage. Such cells can be, for example, grown under standard tissue culture conditions and then added to the ear cartilage or acellular ear cartilage. In another embodiment, the cells can be grown in and/or on an ear cartilage or acellular ear cartilage in tissue culture. Cells grown in and/or on an ear cartilage or acellular ear cartilage in tissue culture can have been obtained directly from an appropriate donor (e.g., the intended recipient or an allogeneic donor) or they can have been first grown in tissue culture in the absence of the ear cartilage or acellular ear cartilage.

In some embodiments, the harvesting of the ear cartilage is performed under aseptic conditions. In some embodiments, the cutting or other manipulation of the ear cartilage or acellular ear cartilage is performed under aseptic conditions. In some embodiments, the decellularization of the ear cartilage is performed under aseptic conditions. In some embodiments, the storage of the ear cartilage or acellular ear cartilage is performed under aseptic conditions.

Physical Properties

As used herein, "tensile force" refers to the stretching forces acting on the material and has two components namely, tensile stress and tensile strain (i.e., the material experiencing the force is under tension, and the forces are trying to stretch it). When a tensile force is applied to a material, it develops a stress corresponding to the applied force, contracting the cross-section and elongating the length. The tensile strain & (epsilon) is expressed as $\varepsilon=\Delta L/L$ (epsilon=deltaL/L). If a compressive force is applied, the compressive strain is expressed as $\varepsilon=-\Delta L/L$ (epsilon=−(deltaL)/L). Based on Hooke's law, the relation between stress and strain is expressed as $\sigma=E\varepsilon$ (sigma=Ex epsilon), where σ (sigma) represents stress, E represents Young's modulus and ε (epsilon) represents strain. On receiving a tensile force, the material expands in the axial direction (longitudinal strain) while contracting in the transverse direction (transverse strain). "Tensile stress" is calculated as Stress (σ)=Force (F)/Area (A) (sigma=F/A). "Tensile strain" is calculated as Strain (ε)=Extension in length (ΔL)/Length (L) (epsilon=deltaL/L).

As used herein, "Young's modulus" or "the Young modulus" is a mechanical property that measures the stiffness of a solid material. It defines the relationship between stress (force per unit area) and strain (proportional deformation) in a material in the linear elasticity regime of a uniaxial deformation. It is typically represented by "E," but can also be represented by "Y." Young's modulus can be calculated as $E=\sigma/\varepsilon$ (E=sigma/epsilon), where σ (sigma) is the uniaxial stress or uniaxial force per unit surface and ε (epsilon) is the strain or proportional deformation (change in length divided by original length). E and σ (sigma) have units of pressure, while ε (epsilon) is dimensionless. Young's moduli are often sufficiently large that they are expressed not in pascals but in megapascals (MPa or $N/mm^2$) or gigapascals (GPa or $kN/mm^2$).

As used herein, the term "stretchiness" refers generally to the ability of tissue or a tissue matrix to stretch or expand under an applied tensile stress, typically plotted as a factor vs. tensile strain. "Tensile stress," measured in megapascals ("MPa") is defined as $S=F/A_o$ (S=F/Ao), wherein F is the tensile force, and Ao is the cross-sectional area of the test sample. "Tensile strain" is defined as $(L_f-L_o)/L_o$ ((Lf−Lo)/Lo) or $\Delta L/L_o$ (delta/Lo), wherein $L_o$ (Lo) is the original length of the tissue matrix, $L_f$ (Lf) is the length of the tissue matrix under a tensile stress, and ΔL (deltaL) is the change in length that the tissue matrix experiences (i.e., $L_f-L_o=\Delta L$ [Lf−Lo=deltaL). In addition, as used herein, "percent extension" is defined as $(L_f-L_o)/L_o\times100\%$ ((Lf−Lo)/L×100%) or $\Delta L/L_o\times100\%$ (deltaL/Lo×100%) and thus is used interchangeably with the term "tensile strain" herein.

On a graph in which the ordinate represents tensile stress in megapascals (MPa) and the abscissa represents tensile strain, the non-linear relationship comprises three well-defined tensile response phases. The first phase is the toe region; the second phase corresponds to the extension of collagen fibrils under stress; and the last phase results from the yielding and final breaking of the tissue material. The stretchiness of tissue may be represented by the length of the toe region, which is determined by extrapolating the second phase of the curve to intercept the x-axis. This can be done mathematically using the linear equation y=a+bx. The x-axis intercept is −a/b.

Alternatively, the comparison between the tensile strain (or percent extension) of a modified ear cartilage-derived preparation and an ear cartilage sample under a small force of about 5 newtons/cm is provided as a method for comparing the stretchiness of the modified ear cartilage-derived preparation and the ear cartilage sample.

As used herein, a "fully hydrated" cartilage or tissue is a cartilage or tissue containing the maximum amount of bound and unbound water that it is possible for that cartilage or tissue to contain under atmospheric pressure. In comparing the amounts of water (unbound and/or bound) in two or more cartilage samples that are fully hydrated, measurements for the two (or more) cartilage samples must be made at the same temperature. "Bound water" in a cartilage is the water in the cartilage whose molecular mobility (rotational and translational) is reduced (compared to pure bulky water) due to molecular interactions (e.g., hydrogen bonding) between the water and cartilage molecules and/or other phenomena (e.g., surface tension and geometric restriction) that limit the mobility of the water in the cartilage. "Unbound water" within the cartilage has the same molecular mobility properties as bulky water in dilute aqueous solutions such as, for example, biological fluids. (As used herein, a "partially hydrated cartilage" is cartilage that contains, at atmospheric pressure, less than 100% but more than 30% (e.g., more than: 35%; 40%; 45%; 50%; 55%; 60%; 65%; 70%; 75%; 80%; 85%; 90%; 95%; 97%; 98%; or 99%) of the unbound and/or bound water that the same cartilage would contain at atmospheric pressure when fully hydrated; again measurements of water amounts in the partially hydrated and fully hydrated cartilage should be made at the same temperature.)

In some embodiments, the cartilage or acellular cartilage is fully hydrated until the moment of testing. In some embodiments, the cartilage or acellular cartilage is maintained at physiologic humidity and temperature during testing.

Elastase treatment produces a modified ear cartilage having a decreased elasticity and/or increased stretchiness relative to the untreated ear cartilage. If an upper or lower eyelid in a vertebral subject has been identified (e.g., by a medical professional such as a physician) as being in need of repair or replacement, then the resulting modified ear cartilage can be placed in or on the upper or lower eyelid for reconstruction (e.g., placed in place of the tarsus, either upper or lower, between the conjunctiva and the orbicularis oculi muscle). Without wishing to be bound to theory, it is believed that elastase treatment breaks peptide bonds in the ear cartilage to produce a modified ear cartilage with a disrupted elastin network. Typically, a sufficient number of peptide bonds are broken to produce some degree of reduced stretchiness in the mATM relative to the ATM. Typically, the number of peptide bonds that are broken is sufficient to the extent that the percent extension (or strain) of mATM under a specific amount of tensile force is less than 95% (e.g., less than: 95%; 90%; 85%; 80%; 75%; 70%; 65%; 60%; 55%; 50%; 45%, 40%, 35%, 30%, 25%, 20%, 15%, 10%, 5% or 2%) of the percent extension (or strain) of ATM under the same amount of tensile force.

After cutting the ear cartilage into strips, testing of tensile force of the cartilage before elastase treatment and/or following the washing step can be performed by methods known in the art. In a non-limiting example, a horizontally mounted microtensile load cell incorporating a linear motor (IBEX ENGINEERING™, Newbury Park, CA) and a strain gauge (LSB200, FUTEK™, Irvine, CA) with 5 mN force resolution is used. This apparatus incorporates a heated water bath, creating a physiologic temperature and humidity during testing. The cross-section of each specimen is tested using an optical coherence tomography (OCT) scanner (THORLABS™ Inc., Newton, NJ), allowing measurement of the mean specimen cross section of each sample for stress calculation. Young's modulus (YM) is a measure of stiffness (see, e.g., Shin et al., Finite Element Biomechanics of Optic Nerve Sheath Traction in Adduction. J. Biomech. Eng. (2017) 139(10): 101010; http://biomechanical.asmedigital-collection.asme.org/article.aspx?doi=10.1115/1.4037562). Specimens are preloaded with 0.05 N stress to avoid tissue laxity, then elongated at 0.1 mm/s as tensile force is recorded until failure signaled by an abrupt decrease in tension and visible rupture. A stress-strain plot is created, and YM computed as the slope of the curve in the linear region.

After cutting in to strips, mechanical indentation may be performed. In a non-limiting example a horizontal tensile loads cell incorporating a linear motor (Ibex Engineering, Newbury Park, CA) and a force sensor (LSB200, FUTEK, Irvine, CA) having 5 mN resolution, and a spherical indenter, 0.3 mm diameter may be used for indentation. See, for example, Shin et al., 2020, Curr Eye Res. 45(7):854-863. Young modulus (MPa) may be calculated using the Hertzian method (Suo et al, *Soft Matter,* 2012, 8, 1492).

In some embodiments, the instantaneous Young modulus of the strip following washing is between about 100-1000 MPa, such as between about 100 and 500 MPa, between about 100 and 200 mPa, between about 100 and 300 mPa, between about 100 and 400 MPa; and the equilibrium Young modulus of the strip following washing is between about 1 and 10 MPa, such as between about 1 and 5 MPa, between about 1 and 2 MPa, between about 5 and 10 MPa. In some embodiments, the Young modulus of the strip (instantaneous and/or equilibrium) is reduced from the untreated value at least 10 fold. In some embodiments, the Young modulus of the strip (instantaneous and/or equilibrium) is reduced from the untreated value at least 10 fold to at least 100 fold. In some embodiments, the Young modulus of the strip (instantaneous and/or equilibrium) is reduced from the untreated value at least 100 fold.

Medically, an "abrasion" is a type of open wound caused by rubbing against a rough surface. It may be called a scrape or a graze. Abrasion injuries most commonly occur when the skin, cornea, or other surface comes into moving contact with a rough surface, causing a grinding or rubbing away of the upper layers of the epidermis, cornea, or other surface, respectively. The "cornea" is the transparent front part of the eye that covers the iris, pupil, and anterior chamber. The cornea, with the anterior chamber and lens, refracts light, with the cornea accounting for approximately two-thirds of the eye's total optical power. In humans, the refractive power of the cornea is approximately 43 diopters. A "corneal abrasion" or "corneal epithelial defect" is a superficial scratch or other epithelial damage on the cornea of the eye. Symptoms include, but are not limited to, pain, tearing of the eye, a gritty feeling in the eye, redness, light sensitivity, and headache and may also result in iritis (an inflammation of the cornea) or leave the subject susceptible to infection. Repeated corneal abrasion may result in permanent damage to the cornea, and therefore, permanent damage to the subject's vision.

In some embodiments, the abrasiveness of the ear cartilage to be used as a replacement eyelid is examined prior to implanting of the treated cartilage on the recipient's eye. In some embodiments, the replacement eyelid is examined following implanting of the treated cartilage on the recipient's eye (e.g., to ensure that it is not damaging the eyelid). In some embodiments, the abrasiveness testing is performed under aseptic conditions.

In a non-limiting example, if the underlying cornea appears to have epithelial damage, as demonstrated by punctate [indicating mild damage] or confluent [indicating severe damage] epithelial staining on slit lamp examination, using staining with fluorescein and a cobalt blue filtered light source, or Lissamine green or Rose Bengal with an unfiltered light source, that condition is then referred to as a "corneal abrasion" or a "corneal epithelial defect," respectively. A "slit lamp" (e.g., HENRY SCHEIN™ Medical, ZEISS™ Lamp Slit #1313585) is an instrument consisting of a high-intensity light source that can be focused to shine a thin sheet of light onto and into the eye to facilitate an examination of the eye surface, anterior segment and posterior segment of the human eye. Structures which may be examined include the eyelid, sclera, conjunctiva, iris, natural crystalline lens, and cornea. A second, hand-held lens is used to examine the retina. Fluorescein staining (e.g., HENRY SCHEIN™ Medical, BIOGLO™ #1372849) uses orange dye (fluorescein; 3',6'-dihydroxyspiro[isobenzofuran-1(3H), 9'-[9H]xanthen]-3-one)) and a cobalt blue light to detect damage to the corneal epithelium. Lissamine green staining uses Lissamine green (e.g., HENRY SCHEIN™ Medical, #1245415), an acidic, synthetically produced, organic dye, as a stain to diagnose ocular surface disease (including damage to the cornea). Rose Bengal staining (e.g., AMCON™ #PO-5600) uses the sodium salt of Rose Bengal (4,5,6,7-tetrachloro-2',4',5',7'-tetraiodofluorescein) to stain damaged conjunctival and corneal cells and thereby identify damage to the eye. "Negative staining" occurs in places where the stain runs off elevations in the cornea, rendering the elevated area unstained relative to the surrounding areas. Negative staining highlights subtle corneal irregularities, while punctate staining indicates mild damage and confluent staining indicates severe damage to the corneal epithelial layer. Following implantation of the cartilage and integration into the eyelid, the patient may be tested for corneal abrasions to confirm that the grafted cartilage in the eyelid does not cause damage to the cornea.

In some embodiments, a small portion of the elastase-treated cartilage may be excised (from the portion intended to be implanted in the eyelid) and subjected to histopathologic examination, e.g., with a stain that shows elastin such as Verhoeff-Van Gieson (VVG) stain (also known as Verhoeff's stain or Verhoeff's elastic stain [VEG]) or Masson's Trichrome (Masson Trichrome) stain.

Masson's Trichrome (Masson Trichrome) is a three-color staining protocol used in histology. In some embodiments, Masson's Trichrome stains produce red keratin and muscle fibers, blue or green collagen and bone, light red or pink cytoplasm, and dark brown to black cell nuclei. In some embodiments, the fixed sample is immersed into Weigert's iron hematoxylin, and then into each of three different solutions (A, B, and C). In some embodiments, Weigert's hematoxylin, which stains the nuclei, comprises a sequence of three solutions: ferric chloride in diluted hydrochloric acid, hematoxylin in 95% ethanol, and potassium ferricyanide solution alkalized by sodium borate. In some embodiments, Solution A (plasma stain) contains acid fuchsin, Xylidine Ponceau, glacial acetic acid, and distilled water. In some embodiments, other red acid dyes can be used (e.g., the Biebrich scarlet in Lillie's trichrome) in Solution A. In some embodiments, Solution B comprises phosphomolybdic acid in distilled water. In some embodiments, Solution C (fiber stain) comprises Light Green SF yellowish. In some embodiments, Solution C, which stains collagen, comprises Fast Green FCF. In some embodiments in which blue is preferred to green, methyl blue or water blue is substituted.

Verhoeff's stain, also known as Verhoeff's elastic stain (VEG) or Verhoeff-Van Gieson stain (VVG), is a histology staining protocol used to demonstrate normal or pathologic elastic fibers. Verhoeff's stain forms a variety of cationic, anionic, and non-ionic bonds with elastin, the main constituent of elastic fiber tissue. Elastin has a strong affinity for the iron-hematoxylin complex formed by the reagents in the stain and will hence retain dye longer than other tissue elements, thereby permitting elastin to remain stained, while remaining tissue elements are decolorized. In some embodiments, sodium thiosulfate is used to remove excess iodine and a counterstain (most often Van Gieson's stain) is used to contrast the principal stain. Typically, elastic fibers and cell nuclei are stained black, collagen fibers are stained red, and other tissue elements including cytoplasm are stained yellow. In some embodiments, components of Verhoeff's stain include hematoxylin, iron(III) chloride, Lugol's iodine, van Gieson's stain, acid fuchsin, picric acid, and sodium thiosulfate.

In some embodiments, a combination of Masson's Trichrome and Verhoeff's elastic stain is used.

Elastase Treatment

As used herein, the term "elastase treatment" refers generally to exposing an ear cartilage sample or acellular ear cartilage sample (or samples) to elastase in a manner that disrupts the elastase network of the tissue thereby reducing the stiffness of the tissue sample(s). Elastase treatment typically is performed any time after (e.g., immediately after, hours after or days after) an ear cartilage sample has been harvested and optionally decellularized. As indicated above, it can also be performed on ear cartilage samples that have been decellularized and then stored frozen or freeze-dried for long periods of time (e.g., several weeks, months, or even years). Alternatively, it can also be performed on ear cartilage samples that have been harvested and then stored frozen or freeze-dried for long periods of time (e.g., several weeks, months, or even years).

As used herein, "elastase" is a serine protease enzyme from the class of proteases (peptidases) that break down proteins. Elastase breaks down elastin, an elastic fiber that, together with collagen, determines the mechanical properties of connective tissue, in addition to some antibacterial and antiviral activities. Elastin breakdown is accomplished through the cleavage of peptide bonds in the target proteins, particularly peptide bonds on the carboxyl side of small, hydrophobic amino acids, such as glycine, alanine, and valine. Elastase is inhibited by the acute-phase protein α1-antitrypsin (alpha1-antitrypsin; A1AT), which is secreted by the liver cells into the serum, and which binds almost irreversibly to the active site of elastase and trypsin.

Elastase breaks down elastin, an elastic fiber that, together with collagen, determines the mechanical properties of connective tissue. Elastin is usually associated with other proteins in connective tissues. Elastic fiber in humans is a mixture of amorphous elastin and fibrous fibrillin, both of which are primarily made of smaller amino acids such as glycine, valine, alanine, and proline. Collagen is the main structural protein in the extracellular matrix in the various connective tissues in the body and is the most abundant protein in mammals, consisting of amino acids bound together to form a triple helix of elongated fibril known as a collagen helix.

Elastase may be obtained from any of a wide variety of sources. It can thus be obtained from animal (e.g., mammalian such as porcine), plant, or microbial (e.g., bacterial) sources. Alternatively, elastase may be obtained via protein expression of a recombinant nucleic acid expression vector in a wide range of systems. Use of a human elastase (e.g., recombinant human elastase) for this purpose is embodied herein.

Elastase from hog pancreas, CAS Number 39445-21-1, Sigma-Aldrich, catalog number E7885, may be used for the purposes described herein.

In humans, eight elastase genes have been classified into four groups: (1) five chymotrypsin-like elastase family (CELA) members (member 1 [CELA1], member 2A [CELA2A], member 2B [CELA2B], member 3A [CELA3A], and member 3B [CELA3B]); (2) one chymotrypsin family member (chymotrypsin C [CTRC]); (3) one neutrophil family member (neutrophil elastase [ELANE]); and (4) one macrophage family member (macrophage metalloelastase [MMP12]).

In some embodiments, the elastase comprises chymotrypsin-like elastase 1 (CELA1), chymotrypsin-like elastase 2A (CELA2A), chymotrypsin-like elastase 2B (CELA2B), chymotrypsin-like elastase 3A (CELA3A), chymotrypsin-like elastase 3B (CELA3B), chymotrypsin C elastase (CTRC), neutrophil elastase (ELANE), or macrophage metalloelastase (MMP12) or a functional fragment or functional variant of any of these or a combination thereof. In some embodiments, the elastase comprises neutrophil elastase (ELANE) or a functional fragment or a functional variant thereof. See, for example, https://www.uniprot.org/uniprot/P00772.

Additional specific non-limiting examples of elastases that can be used in the methods of the present disclosure are the following:

(a) Porcine pancreatic elastase (Enzyme Commission #EC 3.4.21.36) (pancreatopeptidase E), which is a single polypeptide chain of 240 amino acid residues and contains four disulfide bridges. It has a broad specificity and cleaves proteins at the carboxyl side of small hydrophobic amino acids such as Ile, Gly, Ala, Ser, Val, and Leu. It also hydrolyzes amides and esters. Porcine pancreatic elastase is unique among proteases in its ability to hydrolyze native elastin, a substrate not attacked by trypsin, chymotrypsin, or pepsin. By adding soybean trypsin inhibitor and kallikrein inhibitor, its proteolytic activity, but not its elastolytic activity, is suppressed. A non-limiting example of porcine pancreatic elastase (*Sus scrofa*) is chymotrypsin-like elastase family member 1 (CELA-1) (UniProtKB-P00772 (CELA1_PIG); https://www.uniprot.org/uniprot/P00772), as follows in Table 1:

TABLE 1

Porcine elastase (UniProtKB-P00772).

| Protein | Amino Acid Sequence |
|---|---|
| Porcine chymotrypsin-like elastase family member 1 (CELA-1) | MLRLLVVASL VLYGHSTQDF PETNARVVGG TEAQRNSWPS QISLQYRSGS SWAHTCGGTL IRQNWVMTAA HCVDRELTFR VVVGEHNLNQ NDGTEQYVGV QKIVVHPYWN TDDVAAGYDI ALLRLAQSVT LNSYVQLGVL PRAGTILANN SPCYITGWGL TRINGQLAQT LQQAYLPTVD YAICSSSSYW GSTVKNSMVC AGGDGVRSGC QGDSGGPLHC LVNGQYAVHG VTSFVSRLGC NVTRKPTVFT RVSAYISWIN NVIASN (SEQ ID NO: 1) |

The above sequence is further processed into a mature form.

(b) Human neutrophil (leukocyte) elastase (Enzyme Commission #EC 3.4.21.37), which is also known as lysosomal elastase, neutrophil elastase (ELANE), polymorphonuclear leukocyte elastase, serine elastase, lysosomal elastase, or granulocyte elastase. The 29 KDa serine endoprotease exists as a single 238 amino acid-peptide chain with four disulfide bonds and shares approximately 43% sequence homology with porcine pancreatic elastase. The leukocyte elastase cleaves preferentially on the carboxyl side of valine, but also cleaves to a lesser extent after (i.e., on the carboxyl side of) alanine. Besides elastin, leukocyte elastase cleaves cartilage proteoglycans, collagen types I, II, II and IV, and fibronectin.

(c) Human matrix metalloproteinase-12 (MMP12) (Enzyme Commission #EC 3.4.24.65). MMP-12 is also known as macrophage elastase. It is expressed by a wider range of cells than human leukocyte elastase and is secreted as an inactive enzyme (zymogen). The zymogen is activated by removing the propeptide domain. MMP-12 degrades elastin, collagen IV, laminin, fibronectin, serpins such as alpha-1 proteinase inhibitor, alpha-2 antiplasmin, and plasminogen activator inhibitor-2, but not interstitial collagens.

(d) Microbial elastases, including, but not limited to, *Pseudomonas aeruginosa* elastase, which is a metalloproteinase that hydrolyses insoluble elastin, collagens, immunoglobulins, serum alpha-1-proteinase inhibitor, and alpha-2-macroglobin, laminin and fibrin.

Species that can serve as sources of elastase include, but are not limited to, humans, non-human primates (e.g., monkeys, baboons, or chimpanzees), porcine, bovine, horses, goats, sheep, dogs, cats, rabbits, guinea pigs, gerbils, hamsters, rats, or mice. Other sources of elastase include, but are not limited to, microbial elastases. Other elastases include, but are not limited to, elastases or functional variants and fragments thereof, expressed as recombinant molecules produced by standard recombinant methods employing transformed host cells (e.g., eukaryotic cells, such as mammalian, insect, or fungal, including yeast cells, or prokaryotic cells, such as bacterial cells). In a non-limiting example, the ear cartilage or acellular ear cartilage is human, and the elastase is an elastase capable of breaking down human elastin.

In some embodiments, the elastase comprises a human elastase or functional fragment or variant thereof; a non-human primate elastase or functional fragment or functional variant thereof; a porcine elastase or functional fragment or functional variant thereof; a bovine elastase or functional fragment or functional variant thereof; a goat elastase or functional fragment or functional variant thereof; or a sheep elastase or functional fragment or functional variant thereof. In some embodiments, the elastase comprises human neutrophil elastase (ELANE) or a functional fragment or a functional variant thereof; a porcine pancreatic elastase or a functional fragment or a functional variant thereof; a human matrix metalloproteinase-12 (MMP12) or a functional fragment or a functional variant thereof; or a microbial elastase or a functional fragment or a functional variant thereof. In some embodiments, the elastase comprises a recombinant elastase.

Elastases of interest include: (i) wild-type, full length, mature polypeptides; (ii) functional fragments of (i); (iii) functional variants of (i) and (ii). As used herein, a "fragment" of an elastase polypeptide is a fragment of the corresponding wild-type, full-length, mature elastase that is shorter than the corresponding wild-type, full-length, mature elastase. A variant of an elastase can be a wild-type, full-length, mature elastase, or a fragment of an elastase, that contains one or more internal deletions of 1 to 50, 1 to 25, 1 to 15, 1 to 10, 1 to 8, 1 to 5, or 1 to 3 (e.g., 1, 2, 3, 4, 5, 6, 7, 8, 9, 10, 11, 12, 15, 20, 25, 30, 35, 40, or 50) amino acids, internal or terminal additions of any number of amino acids (e.g., the same numbers given above for internal deletions), or not more than 30 (e.g., not more than: 25; 20; 15; 12; 10; 9; 8; 7; 6; 5; 4; 3; 2; or 1) amino acid substitution(s). Amino acid substitutions may be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. "Functional" fragments and "functional" variants of an elastase have at least 25% (e.g., at least: 30%; 40%; 50%; 60%; 70%; 80%; 90%; 95%; 97%; 98%; 99%; 99.5%; 100%; or even greater than 100%) of the elastase activity of, the corresponding wild-type, full-length, mature elastase. It is understood from the above that variants can be allelic variants.

In some embodiments, proteolytic inhibitors (e.g., soybean trypsin inhibitor and kallikrein inhibitor) can be included in the elastase-containing media used to treat ATM in order to decrease its broad, non-specific proteolytic activity but retain all or a substantial level (e.g., >40%, >50%, >60%, >70%, >80%, >90%, >95%, >98%, or >99%) of its non-specific proteolytic activity. In addition, functional variants of elastase that, for example, have reduced non-specific proteolytic activity but retained, minimally reduced, or even enhanced elastolytic activity can be useful.

In one embodiment of the invention, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

As used herein, in one embodiment the term "amino acid" refers to naturally occurring and synthetic α (alpha), β (beta), γ (gamma), or δ (delta) amino acids, and includes but is not limited to, amino acids found in proteins, i.e., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "conservatively modified variants" applies to both amino acid and nucleic acid sequences. "Amino acid variants" refers to amino acid sequences. With respect to particular nucleic acid sequences, conservatively modified variants refer to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds, or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306-1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

All the elastase wild-type polypeptides, fragments, and variants (referred to collectively below as "elastase polypeptides") described above can be obtained from any relevant natural source by standard biochemical and chemical methods.

Alternatively, they can be recombinant molecules produced by standard recombinant methods employing transformed host cells (e.g., eukaryotic, such as mammalian, insect, or fungal, including yeast, cells, or prokaryotic cells, such as bacterial cells). Such recombinant methods are well known in the art.

In some embodiments, the size of a recombinant polynucleotide plasmid may affect the number and efficacy of transcription and translation. In some embodiments, the size of a plasmid comprises about 2000 bp-9000 bp. In some embodiments, the size of a plasmid comprises about 3000 bp-8000 bp. In some embodiments, the size of a plasmid comprises about 3000 bp-7000 bp. In some embodiments, the size of a plasmid comprises about 3000 bp-6000 bp. In some embodiments, the size of a plasmid comprises about 3000 bp-5000 bp.

In some embodiments, the size of a plasmid comprises about 2000 bp, 3000 bp, 4000 bp, 5000 bp, 6000 bp, 7000 bp, 8000 bp, or 9000 bp. Plasmids comprising expression vectors are well known in the art, wherein a skilled artisan would be able to design and produce a plasmid able to express an elastase. In some embodiments, the size of a plasmid expressing porcine elastase comprises about 2000 bp, 3000 bp, 4000 bp, 5000 bp, 6000 bp, 7000 bp, 8000 bp, or 9000 bp.

The term "polynucleotide" as used herein encompasses single-stranded or double-stranded nucleic acid polymers. In certain embodiments, the nucleotides comprising the polynucleotide can be ribonucleotides or deoxyribonucleotides or a modified form of either type of nucleotide. The term "polynucleotide" specifically includes single and double stranded forms of DNA.

The term "operably linked" encompasses components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein encompasses polynucleotide sequences that can affect expression or processing of coding sequences to which they are ligated or operably linked. The nature of such control sequences may depend upon the elements included in the cell-free transcription and translation system. In particular embodiments, transcription control sequences may include a promoter, ribosomal binding site, and transcription termination sequence. In some embodiments, transcription control sequences may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The elastase polypeptides can be used in a crude form (e.g., as a cell lysate or tissue homogenate), in a semi-purified form, or in a substantially pure form. In some embodiments, they may be isolated. The term "isolated elastase polypeptide," as used herein, refers to an elastase polypeptide that either has no naturally-occurring counterpart or has been separated or purified from components that naturally accompany it, e.g., in tissues such as pancreas, liver, spleen, ovary, testis, muscle, joint tissue, neural tissue, gastrointestinal tissue or tumor tissue; body fluids such as blood, serum, or urine; or cells such as leukocytes, monocytic cells, lymphocytic cells, or microbial cells). Typically, an elastase polypeptide is considered "isolated" when it is at least 70%, by dry weight, free from the proteins and other naturally occurring organic molecules with which it is naturally associated. In various embodiment, a preparation of an elastase polypeptide is at least 80%, at least 90%, or at least 99%, by dry weight, the elastase polypeptide. Since an elastase polypeptide that is chemically synthesized is, by its nature, separated from the components that naturally accompany it, a synthetic elastase polypeptide is "isolated." In addition, an elastase polypeptide, that may be present in culture medium or incubation buffer (used, for example, to treat ear cartilage) due to its presence in mammalian serum (or any other bodily fluid) that the culture medium or incubation buffer contains, is not an isolated elastase polypeptide.

An isolated elastase polypeptide useful for performing the methods of the present disclosure, as indicate above, can be obtained, for example, by extraction from a natural source (e.g., from tissues), by expression of a recombinant nucleic acid encoding the polypeptide, or by chemical synthesis. An elastase polypeptide that is produced in a cellular system different from the source from which it naturally originates is "isolated," because it will necessarily be free of components that naturally accompany it. The degree of isolation or purity can be measured by any appropriate method, e.g., column chromatography, polyacrylamide gel electrophoresis, or HPLC analysis.

In some embodiments, the elastase is a commercially available elastase. At least several preparations of elastase are commercially available, including, but not limited to porcine pancreatic elastase (PROMEGA™ CORPORATION, #9PIV189); porcine pancreatic elastase (SIGMA-ALDRICH™, #E0127, #E0258, #E7885, #324682, or #E1250); or recombinant human neutrophil elastase/ELA2 (R&D SYSTEMS™, #9167-SE, Access. No. P08246). In some embodiments, human pancreatic elastase is used.

Producing a modified ear cartilage or modified aceullar ear cartilage having the desired stretchiness can involve controlling, for example, the duration of exposure and the elastase concentration in the solution to which the tissue sample(s) is exposed. The duration of exposure may be between, for example, about 5 minutes and about 24 hours. In some embodiments, the incubating is from about 5 minutes to about 30 minutes. In some embodiments, the incubating is from about 30 minutes to about 24 hours. In some embodiments, the incubating is about 30 minutes, about 60 minutes, about 90 minutes, about 120 minutes, about 150 minutes, about 180 minutes, about 210 minutes, about 240 minutes, about 270 minutes, about 300 minutes, about 330 minutes, about 360 minutes, about 390 minutes, about 420 minutes, about 450 minutes, about 480 minutes, about 510 minutes, about 540 minutes, about 570 minutes, about 600 minutes, about 630 minutes, about 660 minutes, about 690 minutes, about 720 minutes, about 750 minutes, about 780 minutes, about 810 minutes, about 840 minutes, about 870 minutes, about 900 minutes, about 930 minutes, about 960 minutes, about 990 minutes, about 1020 minutes, about 1050 minutes, about 1080 minutes, about 1110 minutes, about 1140 minutes, about 1170 minutes, about 1200 minutes, about 1230 minutes, about 1260 minutes, about 1290 minutes, about 1320 minutes, about 1350 minutes, about 1380 minutes, about 1410 minutes, or about 1440 minutes. In some embodiments, the incubating is from about 30 minutes to about 180 minutes. In some embodiments, the incubating is from about 5 minutes to about 90 minutes.

In some embodiments, ear cartilage or acellular ear cartilage is treated with buffered elastase solution for about 0.1 hours, 0.25 hours, 0.5 hours, 1 hour, or 3 hours.

The concentration of elastase in solution may be between about 0.1 units/milliliter (U/mL) and 100 units/milliliter of buffer or between about 5 units/milliliter and 50 units/milliliter of buffer. In some embodiments, the concentration of elastase in solution is equivalent to about 10 U/mL of buffer.

As used herein, a "buffered solution" ("buffer solution" or "buffer"; e.g., pH buffer or hydrogen ion buffer) comprises an aqueous solution comprising a mixture of a weak acid and its conjugate base, or vice versa. Its pH changes very little when a small amount of strong acid or base is added to it. Buffer solutions are used as a means of keeping pH at a nearly constant value in a wide variety of chemical applications. In nature, there are many systems that use buffering for pH regulation (e.g., the bicarbonate buffering system is used to regulate the pH of blood). The pH of a solution containing a buffering agent can only vary within a narrow range, regardless of what else may be present in the solution. In biological systems this is a critical condition for an enzyme to function correctly and to prevent denaturation, including irreversible denaturation, of the enzyme. The effective range of a buffer is its "buffer capacity."

Physiologically acceptable buffers for enzymes are well-known in the art. Buffers include, but are not limited to, [tris(hydroxymethyl)methylamino]propanesulfonic acid (TAPS); 2-(bis(2-hydroxyethyl)amino)acetic acid (Bicine); tris(hydroxymethyl)aminomethane) or (2-amino-2-(hydroxymethyl)propane-1,3-diol (Tris); Tris-ethylenediamine tetraacetic acid (Tris-EDTA); N-[tris(hydroxymethyl)methyl]glycine (Tricine); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); dimethylarsenic acid (Cacodylate); or 2-(N-morpholino)ethanesulfonic acid (MES). Other acceptable enzyme buffers are known in the art. In some embodiments, Tris comprises Tris-HCl.

In some embodiments, Tris comprises a Tris base. Tris base is commercially available as TRIZMA™ (SIGMA-ALDRICH™) with a buffering range of pH 7 to pH 9. In some embodiments, it has a buffering range of about pH 7 to about pH 9 or a buffering range of about pH 7.5 to about pH 8.5. In some embodiments, it has a buffering range of about pH 8.0 to about pH 9.0.

In some embodiments, the elastase is administered in a buffered solution. In some embodiments, the buffered elastase solution is at about pH 7 to about pH 10. In some embodiments, the buffered elastase solution is at about pH 8.0 to about pH 9.5. In some embodiments, the buffered elastase solution is at about pH 8.4. In some embodiments, the buffered elastase solution comprises a Tris buffer, pH=8.4.

In some embodiments, elastase treatment is performed at ambient temperatures. As used herein, the term "ambient temperatures" means temperatures between about 20 degrees Celsius (deg. C) to about 25 deg. C (about 20° C. to about 25° C.).

In some embodiments, elastase treatment is performed at incubating temperature. In some embodiments, the incubating is at a temperature of about 25 deg. C to about 37 deg. C (about 25° C. to about 37° C.).

In some embodiments, the amount of buffered elastase solution used to treat an ear cartilage sample or an acellular ear cartilage sample is about 3 milliliters per gram (mL/g) of ear cartilage sample or acellular ear cartilage sample. Other amounts of elastase solution may be acceptable as well. In some embodiments, the amount of buffered elastase solution used to treat an ear cartilage sample or an acellular ear cartilage sample is greater than 3 milliliters per gram (mL/g) of ear cartilage sample or acellular ear cartilage sample.

In some embodiments, the tissue sample(s) and the elastase solution are agitated during at least part of, or all of, the duration of elastase exposure.

In some embodiments, the incubating step is performed under aseptic conditions.

In some embodiments, soybean trypsin inhibitor or another enzymatic inhibitor may be included with the elastase solution to mitigate non-specific enzymatic digestion by contaminating enzymes other than elastase. See for example Kafienah et al., 1998, op. cit.

Following incubation with a buffered elastase solution, the ear cartilage or acellular ear cartilage may be subjected to a rinsing or washing step to remove the elastase.

In some embodiments, the washing comprises a rinse in sterile saline. In some embodiments, the washing comprises multiple rinses in sterile normal saline, phosphate-buffered saline, or another buffer of physiological osmolality.

In some embodiments, the washing comprises a rinse in sterile buffer. In some embodiments, the washing comprises multiple rinses in sterile buffer. In some embodiments, the sterile buffer comprises a buffer identical to the buffer of the buffered elastase solution. In some embodiments, the sterile buffer comprises a different buffer than the buffer of the buffered elastase solution.

In some embodiments, the buffer of the rinsing or washing step comprises an elastase inhibitor. Such elastase inhibitor is selected to inhibit the elastase used in the prior step. As noted herein, the rinsing or washing with an elastase inhibitor may be provided at any step after treatment of the cartilage or cartilage strips with elastase.

Both naturally occurring and synthetic inhibitors of elastase are known. In some embodiments, the elastase inhibitor comprises an isolated naturally occurring elastase inhibitor. In some embodiments, the elastase inhibitor comprises a synthetic elastase inhibitor. In some embodiments, the elastase inhibitor is produced by recombinant methods known in the art. In some embodiments, elastase is inhibited by the acute-phase protein α1-antitrypsin (alpha1-antitrypsin, A1AT). A1AT binds almost irreversibly to the active site of elastase and trypsin. Other commercially available elastase inhibitors include, but are not limited to Alvelestat (MEDCHEMEXPRESS™; AZD9668) neutrophil elastase inhibitor; Sivelestat (MEDCHEMEXPRESS™ ONO5046; LY544349; EI546) human neutrophil elastase competitive inhibitor and rabbit and other leukocyte elastase inhibitor; DMP777 human leukocyte elastase inhibitor (MEDCHEM- EXPRESS™); BAY-85-8501 human neutrophil elastase inhibitor (MEDCHEMEXPRESS™); elastase inhibitor I (CALBIOCHEM™, SIGMA-ALDRICH™; #324692) inhibiting porcine pancreatic elastase; elastase inhibitor II (CALBIOCHEM™, SIGMA-ALDRICH™; #324744); elastase inhibitor III (CALBIOCHEM™, SIGMA-ALDRICH™; #324745); elastase inhibitor IV (CALBIOCHEM™, SIGMA-ALDRICH™; #324759); elastase inhibitor V (CALBIOCHEM™, SIGMA-ALDRICH™; #324761); and other commercially available elastase inhibitors. Any of such elastase inhibitor may be provide in a buffered solution having a pH to optimize the inhibition of elastase in the cartilage. Any combination of two or more elastase inhibitors may be used.

Other non-limiting selections of elastase inhibitors include diisopropyl fluorophosphate, a sulfonyl fluoride such as phenylmethanesulfonyl fluoride, and p-dinitrophenyl diethylphosphate. Solutions containing sodium chloride, sodium iodide, potassium chloride, ammonium sulfate, sodium cyanide, or copper sulfate may also be used to inhibit the enzymatic activity of elastase. In some embodiments, sodium chloride is used at about 30 mM to about 100 mM. In some embodiments, copper sulfate is used at about 10 mM. In some embodiments, copper sulfate (about to about 5 micromolar) in combination with hydrogen peroxide (about 250 to about 1000 micromolar) is used. See also Winkler et al., 1978, Connective Tissue Research 6:89-92.

In some embodiments, the washing step is performed at ambient temperatures. As used herein, the term "ambient temperatures" means temperatures between about 20 deg. C to about 25 deg. C (about 20° C. to about 25° C.).

In some embodiments, the washing step is at a temperature of about 25 deg. C to about 37 deg. C (about 25° C. to about 37° C.).

In some embodiments, the tissue sample(s) and the elastase solution are agitated during at least part of, or all of, the duration of the washing step.

In some embodiments, the washing step is performed under aseptic conditions.

In some embodiments, the washing of the cartilage or cartilage strip may be provided after incubation with the elastase, elastase inhibitor, or both, and any additional washing steps (without elastase or elastase inhibitor) may be performed to prepare the cartilage or cartilage strips prior to implantation. The disclosure is not so limiting as to the number of washing steps, and as to whether the cartilage or cartilage strips are washed or rinsed with buffer between steps. In some embodiments, the cartilage or cartilage strips after elastase treatment are incubated with the elastase inhibitor without a washing or rinsing step in between.

In some embodiments, the ear cartilage donor is from a different individual or a different species than the recipient. In these cases, gamma irradiation may be used to decrease the antigenicity of the cartilage. Following an antigen removal process, such as irradiation, detectability of antigens ought to decrease by approximately a factor of 10 in order to reduce or prevent rejection of the graft. In some embodiments, wherein the elastase is porcine pancreatic elastase and washing comprises rinsing until the detectability of porcine antigens is below a minimum detectable level, such as below about 0.1% to about 10% of the original concentration.

In some embodiments, the method further comprises testing the tensile force of the modified ear cartilage or modified acellular ear cartilage following washing as described above. In some embodiments, the instantaneous Young modulus of the modified ear cartilage or modified acellular ear cartilage following washing is between about 100-1000 MPa, such as between about 100 and 500 MPa, and the equilibrium Young modulus of the strip following washing is between about 1 and 10 MPa, such as between about 1 and 5 MPa.

In some embodiments, the tensile force testing is performed using an indentation method.

In some embodiments, the tensile force testing step is performed under aseptic conditions.

In some embodiments, the abrasiveness of the ear cartilage to be used as a replacement eyelid is examined prior to implanting of the treated cartilage on the recipient's eye. In some embodiments, the replacement eyelid is examined following implanting of the treated cartilage on the recipient's eye. In some embodiments, the abrasiveness testing step is performed under aseptic conditions.

Methods of Production, Kits, and Uses Thereof

In some embodiments, "treating" comprises therapeutic treatment including prophylactic or preventive measures, wherein the object is to prevent or lessen the targeted eyelid condition (including, but not limited to, trauma, disease, or tumor excision) by eyelid replacement (e.g., upper or lower eyelid replacement). Thus, in some embodiments, "treating," "ameliorating," and "alleviating" refer inter alia to delaying progression, expediting remission, inducing remission, augmenting remission, speeding recovery, increasing efficacy of or decreasing resistance to alternative therapeutics, or a combination thereof. In some embodiments, "preventing" refers, inter alia, to delaying the onset of symptoms, preventing relapse to a disease, decreasing the number or frequency of relapse episodes, increasing latency between symptomatic episodes, or a combination thereof. In some embodiments, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In some embodiments, "treating" comprises therapeutic treatment including prophylactic or preventive measures, wherein the object is to prevent or lessen the targeted pathologic condition or disorder, for example to treat or prevent an autoimmune disease, an allergic reaction, a localized infection or an infectious disease, an injury or other damage (including, but not limited to, trauma), a transplant or other surgical site (including, but not limited to, tumor excision), or a symptom thereof, or a combination thereof. Thus, in some embodiments, treating may include directly affecting or curing, suppressing, inhibiting, preventing, reducing the severity of, delaying the onset of, reducing symptoms associated with an autoimmune disease, an allergic reaction, a localized infection or an infectious disease, an injury or other damage, a transplant or other surgical site, or a symptom thereof, or a combination thereof. Thus, in some embodiments, "treating," "ameliorating," and "alleviating" refer inter alia to delaying progression, expediting remission, inducing remission, augmenting remission, speeding recovery, increasing efficacy of or decreasing resistance to alternative therapeutics, or a combination thereof. In some embodiments, "preventing" refers, inter alia, to delaying the onset of symptoms, preventing relapse to a disease, decreasing the number or frequency of relapse episodes, increasing latency between symptomatic episodes, or a combination thereof. In some embodiments, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

A "focus of interest" a "localized environment," or a "localized site" comprises a site in which the disease, reaction, infection, injury, or other medical condition is specific to one part or area of the body; in which a symptom or condition of the medical condition is specific to one part or area of the body; or in which treatment is desired for one part or area of the body (even if the disease, reaction, infection, injury, or other medical condition affects other parts or areas of the body or the body as a whole).

In some embodiments, methods disclosed herein treat a focus of interest of an autoimmune disease, an allergic reaction, a localized site of an infection or infectious disease, a localized site of an injury or other damage, a transplant or other surgical site, or a symptom thereof, or a combination thereof.

In some embodiments, an autoimmune disease, an allergic reaction, a localized infection or an infectious disease, an injury or other damage, a transplant or other surgical site, or a symptom thereof, or a combination thereof, comprises a localized site of an autoimmune disease or allergic reaction, a localized site of an infection or infectious disease, a localized site of injury or damage, a transplant or other surgical site, or another site comprising one or more localized symptoms thereof, or a combination thereof.

In some embodiments, the autoimmune disease includes, for example, but is not limited to, Stevens Johnson syndrome, Ocular cicatricial pemphigoid. In some embodiments, the localized site of an autoimmune disease includes, for example, but is not limited to, an eyelid (e.g., upper or lower eyelid) or eye area; conjunctiva; or eyelid margin. In some embodiments, the allergic reaction includes, for example, but is not limited to, a localized allergic reaction including keratoconjunctivitis, ligneous conjunctivitis, giant papillary conjunctivitis. In some embodiments, the localized site of an infection or the localized site of an infectious disease includes, for example, but is not limited to, a fungal infection (e.g., *Mucor, Rhizopus, Aspergillus*), a bacterial infection (e.g., methicillin-resistant *Staphylococcus aureus, Pseudomonas, Chlamydia, Trachoma*), a viral infection (e.g., varicella-zoster/herpes zoster [shingles], Herpes simplex I [e.g., cold sores/fever blisters], Herpes simplex II [genital herpes], or adenovirus), or a parasitic infection (e.g., an area infected by scabies, Chagas, *Hypoderma tarandi*, amoebae, roundworm, *Toxoplasma gondii*. In some embodiments, the injury or other damage includes, for example, but is not limited to traumatic injury (e.g., resulting from an accident or violence) or chronic injury (e.g., osteoarthritis). In some embodiments, the localized site of injury comprises an eye or eyelid (e.g., upper or lower eyelid) injury, a brow injury, a face injury, a temple injury, a *glabella* injury, an injury to the orbit, or an injury to the eye itself. In some embodiments, the transplant or other surgical site includes, for example, but is not limited to, the site and/or its local environment or surroundings of an eyelid (e.g., an upper or lower eyelid) or eye area, or other transplant, or a surgical site and/or its local environment or surroundings, for, e.g., but not limited to, treatment of surgical trauma, treatment of a condition related to the transplant or surgery, or prevention of infection. In some embodiments, the methods disclosed herein treat one or more symptoms of a disease, reaction, infection, injury, transplant, or surgery. In some embodiments, the methods disclosed herein treat a combination thereof.

As used herein, the terms "composition" and "pharmaceutical composition" may in some embodiments, be used interchangeably having all the same qualities and meanings.

As used herein, an organ or tissue "transplantation" comprises a medical procedure in which an organ or tissue is removed from a human or non-human animal subject donor and placed in the body of a human or non-human animal subject recipient, to replace a diseased, damaged, or missing organ or tissue. As used herein, the transplanted organ or tissue comprises an "organ transplant" or "tissue transplant," respectively, or simply a "transplant." As used here, "transplant rejection" is a complication of organ or tissue transplantation during which the recipient's body has an immune response to the transplanted organ or tissue, possibly leading to transplant failure and the need to immediately remove the organ or tissue from the recipient. When possible, transplant rejection can be reduced through serotyping to determine the most appropriate donor-recipient match and through the use of immunosuppressant drugs.

As used herein, an organ, tissue, or blood "donor" denotes a human or non-human animal from which an organ, tissue, or blood, respectively, is removed and transplanted to another human or non-human animal. Legally, a human donor consents while the human donor is alive or the human donors next of kin assents to the donation after the donor's death or brain-death. As used herein, a "living donor" denotes a donor whose organ, tissue, or blood is removed during the lifetime of the donor, before or after brain-death. As used herein, a "cadaver" denotes the body of a deceased human or non-human animal. As used herein, a "cadaveric donor" or "deceased donor" denotes a donor whose organ, tissue, or blood, is removed after death.

As used herein, a "recipient" denotes a human or non-human animal into whose body the transplanted organ, tissue, or blood is placed, injected, or implanted.

As used herein, an "autograft" or "autotransplant" comprises the transplant of an organ or tissue to the same person. Examples of autografts include, but are not limited to, the transplantation of surplus tissue, tissue that can regenerate, or tissues more desperately needed elsewhere. Sometimes an autograft is done to remove the tissue and then treat it or the subject before returning it. Use of an autograft avoids transplant rejection.

In some embodiments, an autograft comprises a method of reconstructing an eyelid comprising preparing ear cartilage for eyelid reconstruction comprising the steps of: (a) harvesting ear cartilage of a subject from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips, followed by implanting the modified ear cartilage over the eye or on the eyelid of the subject.

As used herein, an "allograft" or "allotransplant" comprises the transplant of an organ or tissue between two genetically non-identical members of the same species. Most human organ and tissue transplants are allografts. Due to the genetic difference between the organ or tissue and the recipient, the recipient's immune system will identify the organ or tissue as foreign and attempt to destroy it, causing transplant rejection. The risk of transplant rejection can be estimated by measuring the Panel reactive antibody level. A limiting factor in tissue allotransplantation for reconstructive surgery deals with the side effects of immunosuppression (metabolic disorders, malignancies, opportunistic infections) which is a predominant issue. In addition, the risk of transmitting infection is very high.

In some embodiments, an allograft comprises a method of reconstructing an eyelid comprising preparing ear cartilage for eyelid reconstruction comprising the steps of: (a) harvesting ear cartilage of a donor from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips, followed by implanting the modified ear cartilage over the eye or on the eyelid of a recipient. In some embodiments, the incubating in buffered elastase solution may be performed before the preparing strips. In some embodiments incubation with an elastase inhibitor may follow elastase treatment. In some embodiments, the donor is screened for malignancy (or malignancies) and/or infection(s) prior to harvesting of the ear cartilage. In some embodiments, the risk of transplant rejection is estimated by measuring the Panel reactive antibody level in the donor and recipient prior to the harvesting step. In some embodiments, the risk of transplant rejection is estimated by measuring the Panel reactive antibody level in the donor and recipient prior to implanting the modified ear cartilage over the eye or on the eyelid of the recipient. In some embodiments, the ear cartilage is decellularized prior to transplant in the recipient. In some embodiments, the recipient undergoes immunosuppression therapy following implantation of the modified ear cartilage.

In some embodiments, the allograft transplant is a cadaveric transplant. In some embodiments, the isograft transplant is a cadaveric transplant. In some embodiments, the donor or cadaver is screened for malignancy (or malignancies) and/or infection(s) prior to harvesting of the ear cartilage. In some embodiments, the risk of transplant rejection is estimated by measuring the Panel reactive antibody level in the donor/cadaver and recipient prior to the harvesting step. In some embodiments, the risk of transplant rejection is estimated by measuring the Panel reactive antibody level in the donor/cadaver and recipient prior to implanting the modified ear cartilage over the eye or on the eyelid of the recipient. In some embodiments, the ear cartilage is decellularized prior to transplant in the recipient. In some embodiments, the recipient undergoes immunosuppression therapy following implantation of the modified ear cartilage.

As used herein, an "isograft," "isotransplant," "syngeneic graft," or "syngeneic transplant" comprises a subset of allografts in which an organ or tissue are transplanted from a donor to a genetically identical recipient (such as an identical twin or a donor and recipient who are identical siblings of a multiple birth). Isografts are differentiated from other types of transplants because while they are anatomically identical to allografts, they do not trigger an immune response, although there is still the risk of transmission of malignancy or infectious disease(s).

In some embodiments, an isograft comprises a method of reconstructing an eyelid comprising preparing ear cartilage for eyelid reconstruction comprising the steps of: (a) harvesting ear cartilage of a donor from the scaphoid fossa or the conchal bowl and removing the perichondrium; (b) preparing strips of cartilage of about 4-8 mm×about 10-20 mm and about 0.5 mm thick for the upper eyelid, or about 3-6 mm×about 10-20 mm and about 0.5 mm thick for the lower eyelid; (c) incubating the cartilage strips in a buffered elastase solution; and (d) washing the cartilage strips, followed by implanting the modified ear cartilage over the eye or on the eyelid of a genetically identical recipient. In some embodiments, the incubating in buffered elastase solution may be performed before the preparing strips. In some embodiments incubation with an elastase inhibitor may follow elastase treatment. In some embodiments, the donor and the recipient are identical twins. In some embodiments, the donor and the recipient are identical siblings of a multiple birth. In some embodiments, the donor is screened for malignancy (or malignancies) and/or infection(s) prior to harvesting of the ear cartilage.

As used herein, a "xenograft" or "xenotransplant" comprises a transplant of an organ or tissue from one species to another. However, xenotransplantation is a potentially dangerous type of transplant due to the increased risk of non-functional compatibility, rejection, and disease carried in the tissue, including the "jumping" of a disease of one species into another, previously immune, species. "Xenograft" or "xenotransplant" also refers to the transplant of an organ, tissue, or cells from an animal of a first species into an animal of a second species to produce or grow an organ or tissue for transplant into the same animal or a different animal of the first species.

As used herein, "species" is the basic unit of classification and a taxonomic rank of an organism, as well as a unit of biodiversity. A "species" is often defined as the largest group of organisms in which any two individuals of the appropriate sexes or mating types can produce fertile offspring, typically by sexual reproduction.

"Xenozoonosis," also known as "zoonosis" or "xenosis," is the transmission of infectious agents between species via xenograft. Baboons, pigs, and birds, and to a lesser extent cats, carry myriad transmittable agents that are harmless in their natural host, but extremely toxic and deadly in humans. HIV is an example of a disease believed to have jumped from monkeys to humans. Researchers also do not know if an outbreak of infectious diseases could occur and if they could contain the outbreak even though they have measures for control. Another obstacle facing xenotransplants is that of the body's rejection of foreign objects by its immune system. These antigens (foreign objects) are often treated with powerful immunosuppressive drugs that could, in turn, make the patient vulnerable to other infections and actually aid the disease.

Endogenous retroviruses are remnants of ancient viral infections, found in the genomes of most, if not all, mammalian species. Integrated into the chromosomal DNA, they are vertically transferred through inheritance. Due to the many deletions and mutations they accumulate over time, they usually are not infectious in the host species, however the virus may become infectious in another species. Porcine endogenous retroviruses (PERVS) were originally discovered as retrovirus particles released from cultured porcine kidney cells. Most breeds of swine harbor approximately 50 PERV genomes in their DNA. Although it is likely that most of these are defective, some may be able to produce infectious viruses so every proviral genome must be sequenced to identify which ones pose a threat. In addition, through complementation and genetic recombination, two defective PERV genomes could give rise to an infectious virus. There are three subgroups of infectious PERVs (PERV-A, PERV-B, and PERV-C). Experiments have shown that PERV-A and PERV-B can infect human cells in culture, although to date no experimental xenotransplantations have demonstrated PERV transmission. Pig cells have been engineered to inactivate all 62 PERVs in the genome using CRISPR Cas9 genome editing technology and eliminated infection from the pig to human cells in culture.

In some embodiments, the donor organism is screened for infection(s) prior to harvesting of the ear cartilage. In some embodiments, the donor ear cartilage is screened for infection(s) prior to harvesting of the ear cartilage from the donor organism. In some embodiments, the ear cartilage is screened for infection(s) prior to implantation of the modified ear cartilage in the recipient organism. In some embodiments, the risk of transplant rejection is estimated by measuring the Panel reactive antibody level in the donor organism and recipient organism prior to the harvesting step. In some embodiments, the risk of transplant rejection is estimated by measuring the Panel reactive antibody level in the donor organism or donor ear cartilage and recipient prior to implanting the modified ear cartilage over the eye or on the eyelid of the recipient organism. In some embodiments, the ear cartilage is decellularized prior to transplant in the recipient organism. In some embodiments, the recipient organism undergoes immunosuppression therapy following implantation of the modified ear cartilage.

In some embodiments, the elastase is isolated from one organism and used on an ear cartilage to be implanted in a recipient organism of a different species. In some embodiments, the organism from which the elastase is to be isolated is screened for infection(s) prior to the isolation of the elastase.

Species that can serve as donors of tissues or organs for the production of the acellular ear cartilage include, but are not limited to, humans, non-human primates (e.g., monkeys, baboons, gorillas, orangutans, chimpanzees, or bonobos), porcine, bovine, horses, goats, sheep, dogs, cats, rabbits, hares, pikas, guinea pigs, gerbils, hamsters, rats, or mice.

Species that can serve as recipients of acellular ear cartilage include, but are not limited to, humans, non-human primates (e.g., monkeys, baboons, gorillas, orangutans, chimpanzees, or bonobos), porcine, bovine, horses, goats, sheep, dogs, cats, rabbits, hares, pikas, guinea pigs, gerbils, hamsters, rats, or mice.

Species that can serve as sources of elastase include, but are not limited to, humans, non-human primates (e.g., monkeys, baboons, gorillas, orangutans, chimpanzees, or bonobos), porcine, bovine, horses, goats, sheep, dogs, cats, rabbits, hares, pikas, guinea pigs, gerbils, hamsters, rats, or mice.

Members of the Primate order (primates) include, but are not limited to, *Homo sapiens* (humans) and other members of the Haplorhini suborder/Simiiformes infraorder (e.g., monkeys, baboons [*Papio* genus], gorillas [*Gorilla* genus], orangutans [*Pongo* genus], chimpanzees [*Pan troglodytes*], or bonobos [*Pan paniscus*]).

Porcine species include, but are not limited to, members of the *Sus* genus (e.g., *Sus scrofa* [domestic pig, wild boar]).

Bovine species include, but are not limited to, members of the Bovinae subfamily of the Bovidae family. The biological subfamily Bovinde includes a diverse group of 10 genera of medium to large-sized ungulates, including domestic cattle, bison, African buffalo, the water buffalo, and the four-horned and spiral-horned antelopes, including, but not limited to, members of the *Bos, Bubalus, Pseudoryx, Syncerus, Bison, Tragelaphus, Taurotragus, Tetracerus*, and *Boselaphus* genera.

Horse species include, but are not limited to, members of the *Equus* genus (e.g., *Equus ferus* [domestic horse, wild horse]).

Goat and sheep species include, but are not limited to, members of the Caprinae subfamily of the Bovidae family (e.g., *Capra aegagrus* [domestic goat, wild goat]; *Ovis aries* [sheep]).

Dog species include, but are not limited to, members of the Canidae (canid) family, including the *Canus* (canine) genus (e.g., *Canus* lupus [domestic dog, wild dog, wolf], *Canus latrans* [coyote], various species of jackals), as well as various genera of foxes.

Cat species include, but are not limited to, members of the Felidae (felid) family, including the Pantherinae subfamily, such as the *Panthera* genus (e.g., lions, tigers, jaguars, leopards, snow leopards) and the Neofelis subfamily (e.g., clouded leopard), and the Felinae subfamily, such as the *Felis* (feline) genus (e.g., *Felis catus* [domestic cat, feral cat] and various species of wildcats), as well as various genera of cheetahs, caracals, pumas, ocelots, jaguarundi, servals, lynxes, cougars, and the like.

The Lagomorpha order (e.g., rabbits, hares, and pikas) includes members of the Leporidae family (e.g., rabbits, bunnies, hares) and the Ochoronidae family (e.g., pikas).

The Rodentia order (e.g., guinea pigs, gerbils, hamsters, rats, mice) includes members of the *Cavia* (cavies) family (e.g., guinea pigs), the Cricetidae family (e.g., hamsters), and the Muridae (murid) family (e.g., rats [*Rattus rattus* and other members of the *Rattus* genus], mice [*Mus musculus* and other members of the *Mus* genus], and various genera of gerbils).

As used herein, a "connective tissue" comprises one of the four basic types of animal tissue, along with epithelial tissue, muscle tissue, and nervous tissue. It develops from the mesoderm. Connective tissue is found in between other tissues everywhere in the body, including the nervous system. In the central nervous system, the three outer membranes (the meninges) that envelop the brain and spinal cord are composed of connective tissue. All connective tissue consists of three main components: fibers (elastic and collagenous fibers), ground substance and cells. Not all authorities include blood or lymph as connective tissue because they lack the fiber component. All are immersed in the body water. The cells of connective tissue include fibroblasts, adipocytes, macrophages, mast cells and leucocytes. Type I collagen is present in many forms of connective tissue and makes up about 25% of the total protein content of the mammalian body. Connective tissue is any type of biological tissue with an extensive extracellular matrix that supports, binds together, and protects organs. These tissues form a framework, or matrix, for the body, and are composed of two major structural protein molecules: collagen and elastin. There are many different types of collagen protein in each of the body's tissues. Elastin has the capability of stretching and returning to its original length-like a spring or rubber band. Elastin is the major component of ligaments (tissues that attach bone to bone) and skin.

Connective tissue can be broadly classified into connective tissue proper and special connective tissue. Connective tissue proper consists of loose connective tissue and dense connective tissue (which is further subdivided into dense regular and dense irregular connective tissues). Loose and dense connective tissue are distinguished by the ratio of ground substance to fibrous tissue. Loose connective tissue has much more ground substance and a relative lack of fibrous tissue, while the reverse is true of dense connective tissue. Dense regular connective tissue, found in structures such as tendons and ligaments, is characterized by collagen fibers arranged in an orderly parallel fashion, giving it tensile strength in one direction. Dense irregular connective tissue provides strength in multiple directions by its dense bundles of fibers arranged in all directions.

Special connective tissue consists of reticular connective tissue, adipose tissue, cartilage, bone, and blood. Other kinds of connective tissues include fibrous, elastic, and lymphoid connective tissues. Fibroareolar tissue is a mix of fibrous and areolar tissue. Fibromuscular tissue is made up of fibrous tissue and muscular tissue. New vascularised connective tissue that forms in the process of wound healing is termed granulation tissue.

As used herein, a "connective tissue disease" or "collagenosis" comprises any disease that has the connective tissues of the body as a target of pathology. In patients with connective tissue disease, it is common for collagen and elastin to become injured by inflammation (ICT). Many connective tissue diseases feature abnormal immune system activity with inflammation in tissues as a result of an immune system that is directed against one's own body tissues (autoimmunity). Diseases in which inflammation or weakness of collagen tends to occur are also referred to as collagen diseases. Collagen vascular diseases (e.g., vasculitis) can be (but are not necessarily) associated with collagen and blood vessel abnormalities and that are autoimmune in nature. Connective tissue diseases can have strong or weak inheritance risks and can also be caused by environmental factors.

Connective tissue diseases include, but are not limited to, heritable connective tissue disorders (e.g., Marfan syndrome, Ehlers-Danlos syndrome, osteogenesis imperfecta, Stickler syndrome, Alport syndrome, congenital contractural arachnodactyly [Beals syndrome], Loeys-Dietz syndrome); autoimmune connective tissue disorders (e.g., systemic Lupus erythmotosus [SLE], rheumatoid arthritis, scleroderma, Sjögren's syndrome, systemic sclerosis, dermatomyositis, polymyositis, antisynthetase syndrome, mixed connective tissue disease [MCTD], undifferentiated connective tissue disease [UCTD], psoriatic arthritis); connective tissue neoplasms (e.g., sarcomas); and other connective tissue disorders (e.g., Peyronie's disease, scurvy, fibromuscular dysplasia, myxoma or myxomatous degeneration).

In some embodiments, the ear cartilage is from a donor not having a connective tissue disease. In some embodiments, the donor is screened for connective tissue disease(s) prior to harvesting of the ear cartilage. In some embodiments, the donor ear cartilage is screened for connective tissue disease(s) prior to harvesting of the ear cartilage from the donor. In some embodiments, the ear cartilage is screened for connective tissue disease(s) prior to implantation of the modified ear cartilage in the recipient. In some embodiments, the ear cartilage is decellularized prior to transplant in the recipient organism.

As used herein, an "eyelid" comprises a thin fold of skin that covers and protects an eye. The eyelids include an "upper eyelid" or "superior tarsus" and a "lower eyelid" or "inferior tarsus." The levator palpebrae superioris muscle retracts the upper eyelid, exposing the cornea to the outside, allowing light to strike the visual elements of the eye. The orbicularis oculi muscle is a skeletal muscle responsible for eyelid closure. Eyelid closure may be either voluntary or involuntary. The human eyelid features a row of eyelashes along the eyelid margin, which serve to heighten the protection of the eye from dust and foreign debris, as well as from perspiration. "Palpebral" (and "blepharal") means relating to the eyelids. Its key function is to regularly spread the tears and other secretions on the eye surface to keep it moist, since the cornea must be continuously moist. They keep the eyes from drying out when asleep. Moreover, the blink reflex protects the eye from foreign bodies. The appearance of the human upper or lower eyelid often varies between different populations. The prevalence of an epicanthic fold covering the inner corner of the eye account for the majority of East Asian and Southeast Asian populations and is also found in varying degrees among other populations. Separately, but also similarly varying between populations, the crease of the remainder of the eyelid may form either a "single eyelid," a "double eyelid," or an intermediate form. Eyelids can be found in other animals, some of which may have a third eyelid, or nictitating membrane. A vestige of this in humans survives as the plica semilunaris.

The eyelid may be damaged or missing due to trauma, disease, or tumor excision. Trauma may include a variety of injuries and burns. Tumors include both malignant and non-malignant tumors. Diseases include, but are not limited to, a wide range of systemic and localized diseases. Eyelid disorders include, but are not limited to, drooping/twitching (e.g., blepharospasm, blepharoptosis [e.g., myasthenia gravis]), inflammation (e.g., blepharitis, meibomianitis), dermatitis, paralysis (e.g., facial palsy), infection (e.g., stye [hordeolum]), lacrimal duct obstruction, growths/lesions (e.g., chalazion, seborrheic keratosis, actinic keratosis, hidrocystoma, molluscum contagiosum, nevus, xanthelasma, basal cell carcinoma, squamous cell carcinoma, sebaceous carcinoma, melanoma), coloboma, dermatochalasis, ectropion, entropion, trichiasis, and eyelid retraction.

As used herein, "implanting" a graft comprises suturing the graft in place (e.g., in place of the tarsus, either upper or lower, between the conjunctiva and the orbicularis oculi muscle). In some embodiments, the modified ear cartilage is surgically attached to the recipient's levator palpebrae superioris muscle. In some embodiments, the modified ear cartilage is surgically attached to the recipient's existing upper or lower eyelid or to a remnant or portion thereof.

In some embodiments, the implanting of the modified ear cartilage or modified acellular ear cartilage is performed under aseptic conditions.

In some embodiments, the modified ear cartilage is positioned in place of the tarsus. In some embodiments, the modified ear cartilage is positioned between a conjunctiva and an orbicularis oculi muscle in place of the tarsus. In some embodiments, the modified ear cartilage is positioned in place of an upper tarsus. In some embodiments, the modified ear cartilage is positioned in place of a lower tarsus.

In some embodiments, the modified ear cartilage is covered on one surface with a mucosal graft such as buccal or nasal mucosa, to create a composite graft. The mucosa coated surface would contact the eye surface to create a lubricated contact point.

Provided herein are also uses of ear cartilage prepared as described herein for reconstructing an eyelid in a subject in need thereof.

Provided herein are also compositions for reconstructing an eyelid, the composition comprising scaphoid fossa ear cartilage or conchal bowl ear cartilage cut into strips of about 4-8 mm×about 10-20 mm and about 0.5 mm thick for the upper eyelid, or about 3-6 mm×about 10-20 mm and about 0.5 mm thick for the lower eyelid, following removal of the perichondrium, incubated in a buffered elastase solution, and washed, wherein the instantaneous Young modulus of the strip following washing is between about 100-1000 MPa, such as between about 100 and 500 MPa, and the equilibrium Young modulus of the strip following washing is between about 1 and 10 MPa, such as between about 1 and 5 MPa. In some embodiments, the incubating in buffered elastase solution may be performed before the preparing strips. In some embodiments incubation with an elastase inhibitor may follow elastase treatment.

Provided herein are kits for reconstructing an eyelid from an ear cartilage, the kit comprising: (a) a buffered elastase solution; (b) a buffered elastase inhibitor; and (c) optionally, a buffered wash solution.

Unless otherwise indicated, all numbers expressing quantities, ratios, and numerical properties of ingredients, reaction conditions, and so forth used in the specification and claims are to be understood as being modified in all instances by the term "about". All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise or unless the context clearly dictates otherwise. For example, the term "a compound" or "at least one compound" may include a plurality of compounds, including mixtures thereof.

Also as used herein, "at least one" is intended to mean "one or more" of the listed elements. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

"Consisting of" shall thus mean excluding more than traces of other elements. The skilled artisan would appreciate that while, in some embodiments the term "comprising" is used, such a term may be replaced by the term "consisting of", wherein such a replacement would narrow the scope of inclusion of elements not specifically recited. The terms "comprises", "comprising", "includes", "including", "having" and their conjugates encompass "including but not limited to".

The term "about" or "approximately" means within an acceptable error range for the particular value as determined by one of ordinary skill in the art, which will depend in part on how the value is measured or determined. In some embodiments, the term "about" refers to a deviance of between 0.0001-5% from the indicated number or range of numbers. In some embodiments, the term "about" refers to a deviance of between 1-10% from the indicated number or range of numbers. In some embodiments, the term "about" refers to a deviance of up to 25% from the indicated number or range of numbers. In some embodiments, the term "about" refers to +10%.

Throughout this application, various embodiments may be presented in a range format. It should be understood that the description in range format is merely for convenience and brevity and should not be construed as an inflexible limitation on the scope of certain embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Any patent, patent application publication, or scientific publication, cited herein, is incorporated by reference herein in its entirety.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Preparation of Ear Cartilage with Elastase Treatment

An ear cartilage for eyelid reconstruction is prepared for a recipient having undergone trauma, disease, or tumor removal damaging to the eyelid.

Ear cartilage is harvested from the scaphoid fossa or the conchal bowl, and the perichondrium is removed. Smaller pieces of the cartilage are prepared, and the pieces are incubated with a buffered elastase solution. The pieces are then washed to remove the elastase.

Example 2: Preparation of Ear Cartilage with Decellularization and Elastase Treatment An ear cartilage for eyelid reconstruction is prepared for a recipient having undergone trauma, disease, or tumor removal damaging to the eyelid.

Ear cartilage is harvested from the scaphoid fossa or the conchal bowl, and the perichondrium is removed. Smaller pieces of the cartilage are prepared, and the sample is decellularized via a physical, chemical, or enzymatic treatment.

The pieces are incubated with a buffered elastase solution. The pieces are then washed to remove the elastase.

Example 3: Preparation of Ear Cartilage with Elastase and an Elastase Inhibitor An ear cartilage for eyelid reconstruction is prepared for a recipient having undergone trauma, disease, or tumor removal damaging to the eyelid according to Example 1 or Example 2.

During the washing step, the pieces are washed with a solution comprising an elastase inhibitor.

Example 4: Preparation of Ear Cartilage with Elastase, Followed by Testing of Tensile and/or Mechanical Indentation Force An ear cartilage for eyelid reconstruction is prepared for a recipient having undergone trauma, disease, or tumor removal damaging to the eyelid according to any one of Examples 1-3.

Following washing, the tensile and/or mechanical indentation force of the pieces is tested for a Young modulus, the instantaneous Young modulus of the strip following washing is between about 100-1000 MPa, such as between about 100 and 500 MPa, and the equilibrium Young modulus of the strip following washing is between about 1 and 10 MPa, such as between about 1 and 5 MPa.

Additional elastase treatment may be provided if the tensile and/or mechanical indentation force is not yet near or within the optimal range for implantation.

Example 5: Preparation of Ear Cartilage with Elastase Treatment, Followed by Abrasiveness Testing An ear cartilage for eyelid reconstruction is prepared for a recipient having undergone trauma, disease, or tumor removal damaging to the eyelid according to any one of Examples 1-4.

Before elastase treatment and again following washing, the abrasiveness of the pieces is compared, such as by histopathologic examination with a stain that shows elastin (e.g., VVG or Masson's Trichrome staining), and/or following the methods in Example 4.

Example 6: Preparation of Ear Cartilage for Reconstructing an Eyelid

An ear cartilage for eyelid reconstruction is prepared for a recipient having undergone trauma, disease, or tumor removal damaging to the eyelid according to any one of Examples 1-5.

Following washing and optionally testing for tensile force and/or abrasiveness, the modified ear cartilage or modified acellular ear cartilage is used to reconstruct a recipient's eyelid.

Example 7: Preparation of Ear Cartilage for Reconstructing an Upper Eyelid

An ear cartilage for eyelid reconstruction is prepared for a recipient having undergone trauma, disease, or tumor removal damaging to the upper eyelid according to any one of Examples 1-5.

Following washing and optionally testing for tensile force and/or abrasiveness, the modified ear cartilage or modified acellular ear cartilage is used to reconstruct a recipient's upper eyelid.

Example 8: Preparation of Ear Cartilage for Autograft Transplantation for Reconstructing an Eyelid or Upper Eyelid Where the subject has undergone trauma, disease, or tumor removal damaging to the upper eyelid or lower eyelid, ear cartilage from the subject is harvested and prepared according to any one of Examples 1-7.

Following washing and optionally testing for tensile force and/or abrasiveness, the modified ear cartilage is used as an autograft transplant to reconstruct the subject's upper or lower eyelid.

Example 9: Preparation of Ear Cartilage for Allograft Transplantation for Reconstructing an Eyelid or Upper Eyelid A potential living or brain-dead donor is tested for malignancies and diseases, including infectious diseases connective tissue diseases. The potential donor and potential recipient (the potential recipient having undergone trauma, disease, or tumor removal damaging to the eyelid or upper eyelid) are tested for risk of transplant rejection by measuring the Panel reactive antibody level.

An ear cartilage harvested from the donor for eyelid reconstruction in the recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as an allograft transplant to reconstruct the recipient's eyelid or upper eyelid.

Example 10: Preparation of Ear Cartilage for Allograft Transplantation for Reconstructing an Eyelid or Upper Eyelid A potential cadaveric donor or ear cartilage harvested from a living or cadaveric donor (and optionally frozen, freeze-dried, or otherwise stored) is tested for malignancies and diseases, including infectious diseases and connective tissue diseases. The potential cadaveric donor or ear cartilage harvested from a living or cadaveric donor and the potential recipient (the potential recipient having undergone trauma, disease, or tumor removal damaging to the eyelid or upper eyelid) are tested for risk of transplant rejection by measuring the Panel reactive antibody level.

An ear cartilage harvested from the cadaveric donor or ear cartilage harvested from a living or cadaveric donor, for eyelid reconstruction in the recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as an allograft transplant to reconstruct the recipient's eyelid or upper eyelid.

Example 11: Preparation of Ear Cartilage for Isograft Transplantation for Reconstructing an Eyelid or Upper Eyelid A potential living or brain-dead donor is tested for isogeneity with the potential recipient (the potential recipient having undergone trauma, disease, or tumor removal damaging to the eyelid or upper eyelid), as well as for malignancies and diseases, including infectious diseases and connective tissue diseases.

An ear cartilage harvested from the donor for eyelid reconstruction in the isogenic recipient is prepared according to any one of Examples 1-7.

Following washing and optionally testing for tensile force and/or abrasiveness, the modified ear cartilage is used as an allograft transplant to reconstruct the recipient's eyelid or upper eyelid.

Example 12: Preparation of Ear Cartilage for Isograft Transplantation for Reconstructing an Eyelid or Upper Eyelid A potential cadaveric donor or ear cartilage harvested from a living or cadaveric donor (and optionally frozen, freeze-dried, or otherwise stored) is tested for isogeneity with the potential recipient (the potential recipient having undergone trauma, disease, or tumor removal damaging to the eyelid or upper eyelid), as well as for malignancies and diseases, including infectious diseases and connective tissue diseases.

An ear cartilage harvested from the cadaveric donor or ear cartilage harvested from a living or cadaveric donor, for eyelid reconstruction in the isogenic recipient is prepared according to any one of Examples 1-7.

Following washing and optionally testing for tensile force and/or abrasiveness, the modified ear cartilage is used as an isograft transplant to reconstruct the recipient's eyelid or upper eyelid.

Example 13: Preparation of Ear Cartilage for Xenograft Transplantation for Reconstructing an Eyelid or Upper Eyelid A potential living or brain-dead donor of a first species is tested for xenozoonotic diseases (including endogenous retroviruses), malignancies, and other diseases, including infectious diseases connective tissue diseases. The potential first-species donor and potential second-species recipient (the potential second-species recipient having undergone trauma, disease, or tumor removal damaging to the eyelid or upper eyelid) are tested for risk of transplant rejection by measuring, for example the Panel reactive antibody level.

An ear cartilage harvested from the first-species donor for eyelid reconstruction in the second-species recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as a xenograft transplant to reconstruct the second-species recipient's eyelid or upper eyelid.

Example 14: Preparation of Ear Cartilage for Xenograft Transplantation for Reconstructing an Eyelid or Upper Eyelid A potential cadaveric first-species donor or ear cartilage harvested from a living or cadaveric first-species donor (and optionally frozen, freeze-dried, or otherwise stored) is tested for xenozoonotic diseases (including endogenous retroviruses), malignancies, and other diseases, including infectious diseases and connective tissue diseases. The potential cadaveric first-species donor or ear cartilage harvested from a living or cadaveric first-species donor and the potential second-species recipient (the potential second-species recipient having undergone trauma, disease, or tumor removal damaging to the eyelid or upper eyelid) are tested for risk of transplant rejection by measuring the Panel reactive antibody level.

An ear cartilage harvested from the cadaveric first-species donor or ear cartilage harvested from a living or cadaveric first-species donor, for eyelid reconstruction in the second-species recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as a xenograft transplant to reconstruct the second-species recipient's eyelid or upper eyelid.

Example 15: Preparation of Ear Cartilage for Xenograft Transplantation for Reconstructing an Eyelid or Upper Eyelid A potential living or brain-dead donor of a non-human animal species is tested for xenozoonotic diseases (including endogenous retroviruses), malignancies, and other diseases, including infectious diseases connective tissue diseases. The potential non-human donor and potential human recipient (the potential recipient having undergone trauma, disease, or tumor removal damaging to the eyelid or upper eyelid) are tested for risk of transplant rejection by measuring, for example, the Panel reactive antibody level.

An ear cartilage harvested from the non-human donor for eyelid reconstruction in the human recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as a xenograft transplant to reconstruct the human recipient's eyelid or upper eyelid.

Example 16: Preparation of Ear Cartilage for Xenograft Transplantation for Reconstructing an Eyelid or Upper Eyelid A potential cadaveric non-human animal donor or ear cartilage harvested from a living or cadaveric non-human animal donor (and optionally frozen, freeze-dried, or otherwise stored) is tested for xenozoonotic diseases (including endogenous retroviruses), malignancies, and other diseases, including infectious diseases and connective tissue diseases. The potential cadaveric non-human donor or ear cartilage harvested from a living or cadaveric non-human donor and the potential human recipient (the potential human recipient having undergone trauma, disease, or tumor removal damaging to the eyelid or upper eyelid) are tested for risk of transplant rejection by measuring the Panel reactive antibody level.

An ear cartilage harvested from the cadaveric non-human donor or ear cartilage harvested from a living or cadaveric non-human donor, for eyelid reconstruction in the human recipient is prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is used as a xenograft transplant to reconstruct the human recipient's eyelid or upper eyelid.

Example 17: Preparation of Ear Cartilage for Future Transplantation

An ear cartilage is harvested from a donor or ear cartilage harvested from a donor and prepared according to any one of Examples 1-7. Prior to incubating with elastase, the ear cartilage pieces optionally undergo decellularization.

Following washing and optionally testing for tensile force and/or abrasiveness, the modified ear cartilage or modified acellular ear cartilage is stored (e.g., frozen, freeze-dried, or otherwise aseptically stored) or banked for future transplantation.

Example 18: Preparation of Ear Cartilage for Reconstructing a Lower Eyelid

An ear cartilage for eyelid reconstruction is prepared for a recipient having undergone trauma, disease, or tumor removal damaging to the lower eyelid according to any one of Examples 1-5.

Following washing and optionally testing for tensile force and/or abrasiveness, the modified ear cartilage or modified acellular ear cartilage is used to reconstruct a recipient's lower eyelid.

Example 19: Preparation of Ear Cartilage and Methods of Use

With controlled elastase digestion, cartilage can be softened, and can be made less rigid and thus less abrasive to the corneal surface when implanted in the eyelid.

Porcine auricular cartilage (Sierra for Biomedical Science, Whittier, CA) was harvested and stripped gently of most perichondrium. The cartilage was cut in to 1 cm discs. An electronic caliper was used to measure cartilage thickness.

Elastase (CAS Number 39445-21-1, Sigma-Aldrich) reconstituted in Tris buffer, pH 8.0 to a final concentration of 1 U/mL. Cartilage was placed in buffer control or in elastase solution and incubated at room temperature for 24 hours.

Elastin was visualized using electron microscopy and by histopathology (Masson Trichrome). Mechanical indentation was performed using a horizontal tensile loads cell incorporating a linear motor (Ibex Engineering, Newbury Park, CA) and a force sensor (LSB200, FUTEK, Irvine, CA) having 5 mN resolution, and a spherical indenter, 0.3 mm diameter). See, for example, Shin et al., 2020, Curr Eye Res. 45(7):854-863. Young modulus (MPa) was calculated using the Hertzian method (Suo et al, *Soft Matter,* 2012, 8, 1492).

FIG. 1 shows the results of cartilage indentation testing. At a temperature of 37 C, the tip of the indenter, once in contact with the sample surface, was advanced to an indenting depth of 0.15 mm at a nominal loading rate of 0.2 mm/sec. This was followed by a 300 second displacement hold. Young modulus (both instantaneous and equilibrium) measurements were performed as follows: three measurements from three positions (at least 3 mm apart) on each sample of control cartilage and three such measurements from each sample of elastase-treated cartilage. The single-axis logarithmic bar graph depicts the mean Young's modulus (MPa) for experiments comparing such measurements for three control cartilage samples with three elastase-treated samples. E0 represents the Young modulus instantaneously during indentation (time=0), E_inf represents the Young modulus represents Young modulus at equilibrium (time=∞). Compared to control cartilage, elastase treated samples exhibited lower mean (standard deviation) compressive Young modulus, instantaneously [$E_0$] $1.27\times10^2$ ($3.0\times10^2$) vs. $1.18\times10^5$ ($5.58\times10^4$) MPa and at equilibrium [$E_\infty$] $7.19\times10^2$ ($3.4\times10^2$) vs. $2.23\times10^0$ ($7.0\times10^{-1}$) MPa.

Figure 2B:
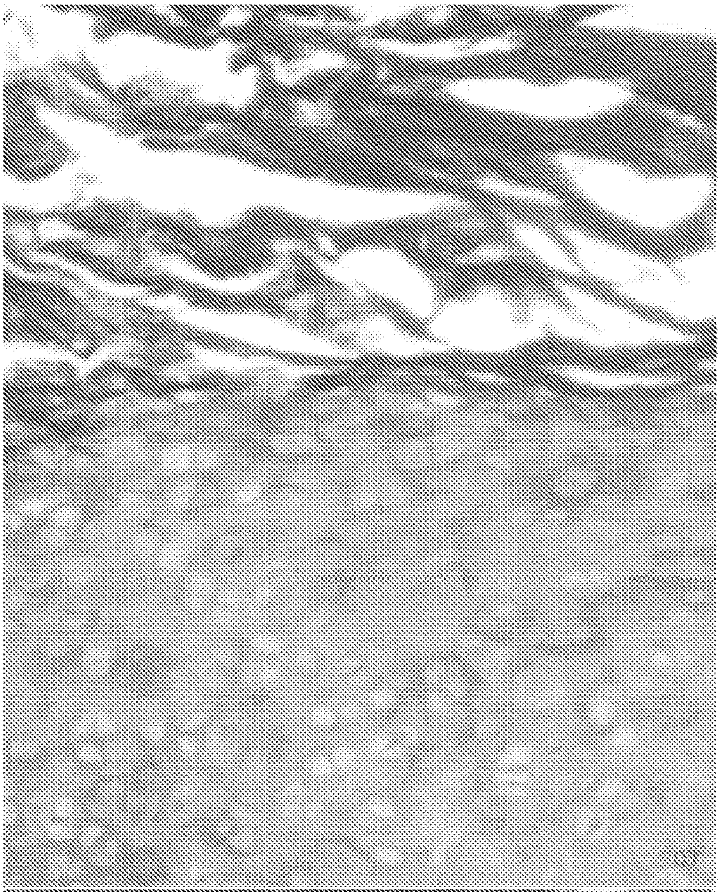
FIGS. 2A-2B show histopathologic images (×40 magnification, Masson's Trichrome stain) of representative control cartilage (FIG. 2A) and elastase-treated cartilage (treated according to protocol in Example 19, see FIG. 2B). These slides highlight the junction between the cartilage (left half of each image) and the perichondrium (right half of each image). Compared to control cartilage, elastase-treated cartilage displayed increased chondrocyte lacunae, along with a decrease in the density of both territorial and interterritorial matrices. Further, elastase treated cartilage displayed clefts and widening of perichondrial lamellae.
Figure 2A:
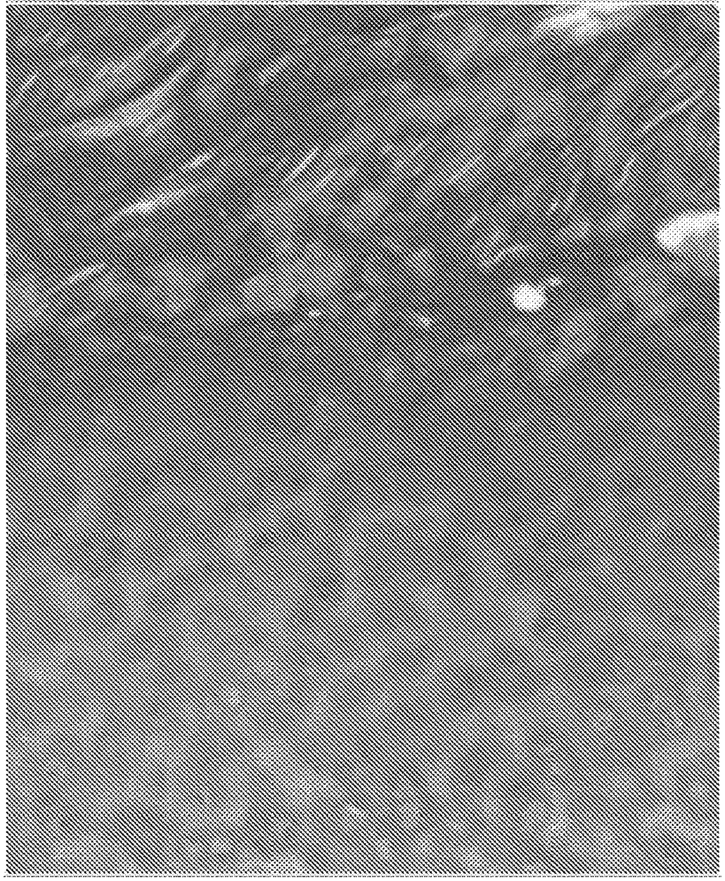

FIGS. 2A-2B show histopathologic images (×40 magnification, Masson's Trichrome stain) of representative control cartilage (FIG. 2A) and elastase-treated cartilage (treated according to protocol in FIG. 1, see FIG. 2B). These slides highlight the junction between the cartilage (left half of each image) and the perichondrium (right half of each image). Compared to control cartilage, elastase-treated cartilage displayed increased chondrocyte lacunae, along with a decrease in the density of both territorial and interterritorial matrices. Further, elastase treated cartilage displayed clefts and widening of perichondrial lamellae.

Figure 3B:
FIG. 3 shows gross appearance of control cartilage (left image) and elastase-treated cartilage (treated according to protocol in FIG. 1, right image). Note the grossly inflexible appearance of the control cartilage and the flexible appearance of the elastase treated cartilage.
Figure 3A:
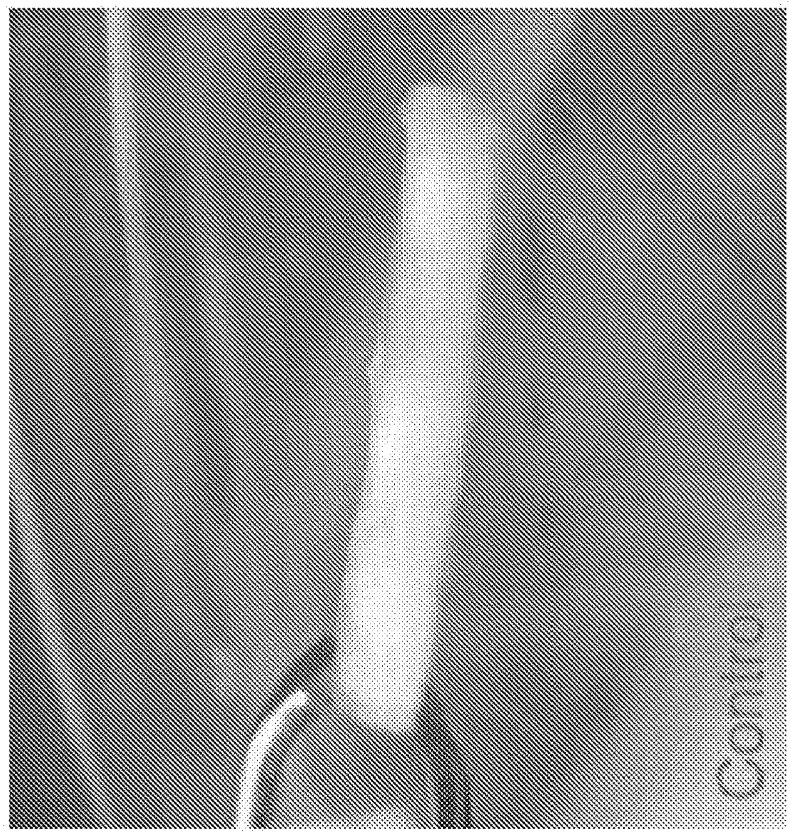

FIG. 3 shows gross appearance of control cartilage (left image) and elastase-treated cartilage (treated according to protocol in FIG. 1, right image). Note the grossly inflexible appearance of the control cartilage and the flexible appearance of the elastase treated cartilage. The difference in flexibility was readily observed during handling of the cartilage and/or pressing the cartilage against a surface. The elastase treated cartilage was clearly more flexible when held at one end by forceps, and on pressing against a surface, the elastase treated cartilage more giving; the control cartilage was less flexible and less giving on pressing upon a surface.

Figure 4B:
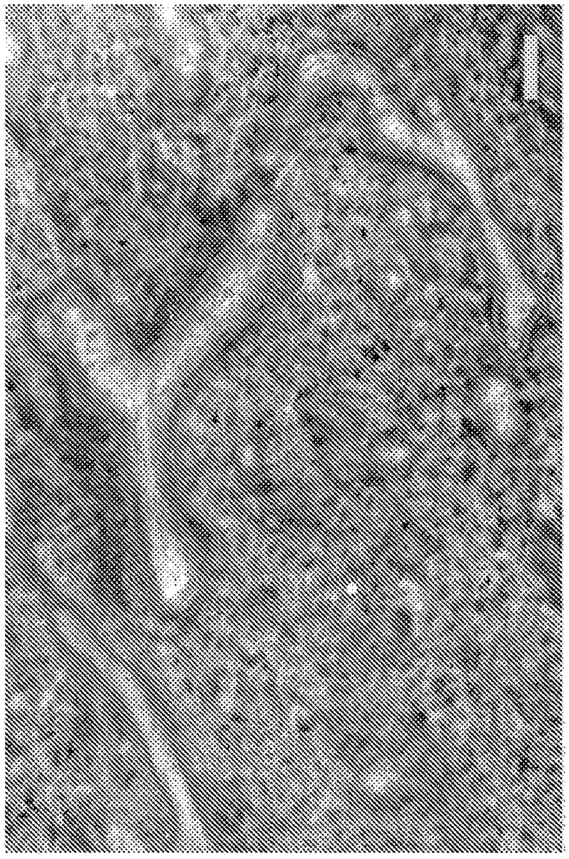
FIG. 4A-4B shows electron microscopic images (×2900 magnification, scale bar is 1 μm) of representative control cartilage (FIG. 4A) and elastase-treated cartilage (treated according to protocol in Example 19, see FIG. 4B). Drawn lines circumscribe the location of elastic fibers. Compared to control cartilage, elastase-treated cartilage demonstrated empty channels in place of elastic fibers.
Figure 4A:
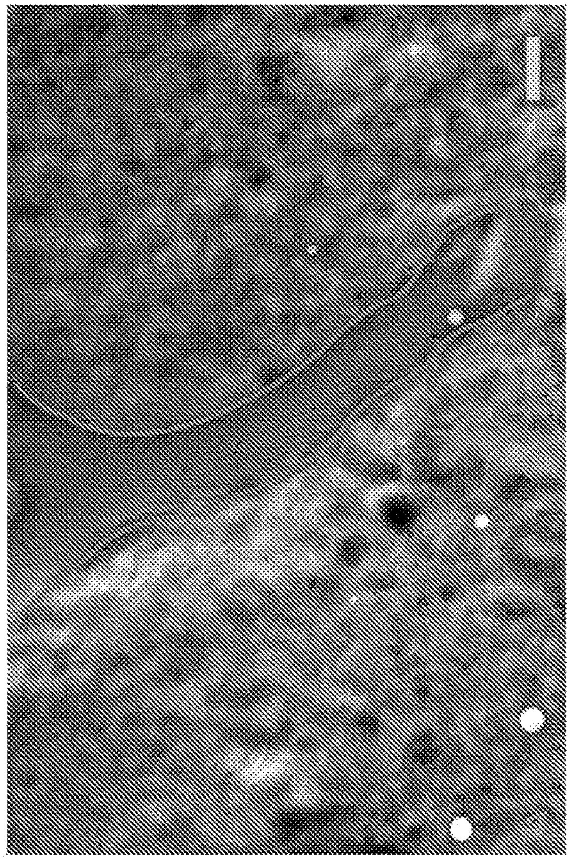

FIG. 4A-4B shows electron microscopic images (×2900 magnification, scale bar is 1 μm) of representative control cartilage (FIG. 4A) and elastase-treated cartilage (treated according to protocol in FIG. 1, see FIG. 4B). Drawn lines circumscribe the location of elastic fibers. Compared to control cartilage, elastase-treated cartilage demonstrated empty channels in place of elastic fibers.

Example 20: Preparation of Ear Cartilage with Elastase Treatment

An ear cartilage for eyelid reconstruction is prepared for a recipient having undergone trauma, disease, or tumor removal damaging to the eyelid.

Ear cartilage is harvested from the scaphoid fossa or the conchal bowl, and the perichondrium is removed. The cartilage is incubated with a buffered elastase solution. The cartilage is washed to remove the elastase, then cut into pieces for implantation.

Example 21: Preparation of Ear Cartilage with Elastase and an Elastase Inhibitor An ear cartilage for eyelid reconstruction is prepared for a recipient having undergone trauma, disease, or tumor removal damaging to the eyelid according to Example 20.

After elastase treatment, the cartilage is washed with a solution comprising an elastase inhibitor.

Example 22: Preparation of Ear Cartilage for Reconstructing an Eyelid

An ear cartilage for eyelid reconstruction is prepared for a recipient having undergone trauma, disease, or tumor removal damaging to the eyelid according to any one of Examples 20-21.

Following washing and optionally testing for tensile force and/or abrasiveness, the modified ear cartilage is used to reconstruct a recipient's eyelid.

While certain features and methods of use thereof have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for preparing ear cartilage for eyelid reconstruction comprising the steps of:

(a) harvesting ear cartilage from the scaphoid fossa or the conchal bowl and removing the perichondrium;

(b) preparing a strip of cartilage of about 4-8 mm×about 10-20 mm and about 0.5 mm thick for the upper eyelid, or about 3-6 mm×about 10-20 mm and about 0.5 mm thick for the lower eyelid;

(c) incubating the cartilage strip in a buffered elastase solution before or after step (b); and (d) washing the cartilage strip.

2. The method of claim 1, wherein the ear cartilage is an autograft, allograft, isograft, or xenograft.

3. The method of claim 1, wherein the ear cartilage is cadaveric.

4. The method of claim 1, wherein the elastase is pancreatic elastase or neutrophil elastase.

5. The method of claim 1, wherein the elastase is human pancreatic elastase, human neutrophil elastase or porcine pancreatic elastase.

6. The method of claim 1, wherein the elastase is equivalent to about 1 to about 10 units/milliliter (U/mL) of buffer.

7. The method of claim 1, wherein the buffer is at about pH 6.0 to about pH 9.5.

8. The method of claim 7, wherein the buffer is about pH 8.0 to about pH 9.5.

9. The method of claim 1, wherein the incubating is from about 5 minutes to about 24 hours, or from about 30 minutes to about 24 hours.

10. The method of claim 1, wherein the incubating is at a temperature of about 25 degrees C. to about 37 degrees C.

11. The method of claim 1, wherein the washing comprises an elastase inhibitor.

12. The method of claim 1, wherein the elastase is porcine pancreatic elastase and washing comprises rinsing until the detectability of porcine antigens is below about 10% of the initial antigenicity.

13. The method of claim 1, wherein the instantaneous Young modulus of the strip following washing is between about 100-1000 MPa, and the equilibrium Young modulus of the strip following washing is between about 1 and 10 MPa.

14. The method of claim 2, wherein when the ear cartilage is an allograft or xenograft, the cartilage is decellularized prior to step c.

15. A method of reconstructing an eyelid comprising implanting ear cartilage prepared in accordance with claim 1.

* * * * *

SEQUENCE LISTING

<160> NUMBER OF SEQ ID NOS: 1

<210> SEQ ID NO 1

-continued

```
<211> LENGTH: 266
<212> TYPE: PRT
<213> ORGANISM: Sus scrofa

<400> SEQUENCE: 1

Met Leu Arg Leu Leu Val Val Ala Ser Leu Val Leu Tyr Gly His Ser
1               5                   10                  15

Thr Gln Asp Phe Pro Glu Thr Asn Ala Arg Val Val Gly Gly Thr Glu
            20                  25                  30

Ala Gln Arg Asn Ser Trp Pro Ser Gln Ile Ser Leu Gln Tyr Arg Ser
        35                  40                  45

Gly Ser Ser Trp Ala His Thr Cys Gly Gly Thr Leu Ile Arg Gln Asn
    50                  55                  60

Trp Val Met Thr Ala Ala His Cys Val Asp Arg Glu Leu Thr Phe Arg
65                  70                  75                  80

Val Val Val Gly Glu His Asn Leu Asn Gln Asn Asp Gly Thr Glu Gln
                85                  90                  95

Tyr Val Gly Val Gln Lys Ile Val Val His Pro Tyr Trp Asn Thr Asp
            100                 105                 110

Asp Val Ala Ala Gly Tyr Asp Ile Ala Leu Leu Arg Leu Ala Gln Ser
        115                 120                 125

Val Thr Leu Asn Ser Tyr Val Gln Leu Gly Val Leu Pro Arg Ala Gly
    130                 135                 140

Thr Ile Leu Ala Asn Asn Ser Pro Cys Tyr Ile Thr Gly Trp Gly Leu
145                 150                 155                 160

Thr Arg Thr Asn Gly Gln Leu Ala Gln Thr Leu Gln Gln Ala Tyr Leu
                165                 170                 175

Pro Thr Val Asp Tyr Ala Ile Cys Ser Ser Ser Ser Tyr Trp Gly Ser
            180                 185                 190

Thr Val Lys Asn Ser Met Val Cys Ala Gly Gly Asp Gly Val Arg Ser
        195                 200                 205

Gly Cys Gln Gly Asp Ser Gly Gly Pro Leu His Cys Leu Val Asn Gly
    210                 215                 220

Gln Tyr Ala Val His Gly Val Thr Ser Phe Val Ser Arg Leu Gly Cys
225                 230                 235                 240

Asn Val Thr Arg Lys Pro Thr Val Phe Thr Arg Val Ser Ala Tyr Ile
                245                 250                 255

Ser Trp Ile Asn Asn Val Ile Ala Ser Asn
            260                 265
```